United States Patent
Fishman

(10) Patent No.: US 10,350,437 B2
(45) Date of Patent: Jul. 16, 2019

(54) ROBOTIC IORT X-RAY RADIATION SYSTEM WITH CALIBRATION WELL

(71) Applicant: Sensus Healthcare, Inc., Boca Raton, FL (US)

(72) Inventor: Kalman Fishman, Boca Raton, FL (US)

(73) Assignee: Sensus Healthcare, Inc., Boca Raton, FL (US)

( * ) Notice: Subject to any disclaimer, the term of this patent is extended or adjusted under 35 U.S.C. 154(b) by 0 days.

(21) Appl. No.: 16/103,241

(22) Filed: Aug. 14, 2018

(65) Prior Publication Data

US 2019/0060674 A1 Feb. 28, 2019

Related U.S. Application Data

(60) Provisional application No. 62/551,417, filed on Aug. 29, 2017.

(51) Int. Cl.
*A61N 5/10* (2006.01)

(52) U.S. Cl.
CPC ......... *A61N 5/1075* (2013.01); *A61N 5/1015* (2013.01); *A61N 5/1048* (2013.01); *A61N 5/1083* (2013.01)

(58) Field of Classification Search
CPC .. A61N 5/1015; A61N 5/1075; A61N 5/1083; A61N 5/1048; A61N 5/1081; A61N 5/1082
USPC .................................................. 378/65, 207
See application file for complete search history.

(56) References Cited

U.S. PATENT DOCUMENTS

| | | | | |
|---|---|---|---|---|
| 4,401,406 A * | 8/1983 | Rovira | ...... | A61N 5/00 212/201 |
| 5,621,214 A * | 4/1997 | Sofield | ...... | G01T 1/185 250/375 |
| 5,635,709 A * | 6/1997 | Sliski | ...... | G01T 1/169 250/252.1 |
| 5,635,721 A * | 6/1997 | Bardi | ...... | A61N 5/01 250/492.3 |
| 6,207,952 B1 * | 3/2001 | Kan | ...... | A61N 5/1048 250/252.1 |
| 6,826,254 B2 * | 11/2004 | Mihara | ...... | A61N 5/10 250/492.3 |

(Continued)

OTHER PUBLICATIONS

International Search Report and Written Opinion dated Oct. 29, 2018 in PCT/US18/46663.

*Primary Examiner* — Allen C. Ho
(74) *Attorney, Agent, or Firm* — Fox Rothschild LLP

(57) ABSTRACT

X-ray delivery system includes a portable base unit to which a first end of a robotic arm is mounted. An X-ray treatment head is disposed on a second end of the robotic arm. The X-ray treatment head includes an X-ray component configured to generate therapeutic radiation in the X-ray wavelength range. A calibration well is disposed at a predetermined location in the portable base unit. The calibration well is comprised of a recess into which the X-ray treatment head can be received and having at least one port through which the X ray treatment head can be inserted by the robotic arm for calibration operations. The calibration well includes a plurality of X-ray radiation sensing elements disposed at distributed locations around a periphery of the calibration well.

20 Claims, 12 Drawing Sheets

(56) References Cited

U.S. PATENT DOCUMENTS

| | | | | |
|---|---|---|---|---|
| 6,977,987 | B2* | 12/2005 | Yamashita | A61N 5/10 378/64 |
| 7,005,623 | B2* | 2/2006 | Neuberger | G01J 1/04 250/205 |
| 7,188,999 | B2* | 3/2007 | Mihara | A61N 5/10 378/197 |
| 7,193,220 | B1* | 3/2007 | Navarro | G01T 1/169 250/252.1 |
| 7,200,203 | B2* | 4/2007 | Cocks | A61N 5/1001 378/119 |
| 7,239,684 | B2* | 7/2007 | Hara | A61N 5/1049 378/65 |
| 7,263,170 | B2* | 8/2007 | Pellegrino | A61N 5/10 378/115 |
| 7,266,176 | B2* | 9/2007 | Allison | A61N 5/1031 378/205 |
| 7,283,610 | B2* | 10/2007 | Low | A61N 5/1027 378/197 |
| 7,356,120 | B2* | 4/2008 | Main | A61N 5/1048 250/252.1 |
| 7,420,160 | B2* | 9/2008 | Delaperriere | G01T 1/169 250/252.1 |
| 7,505,559 | B2* | 3/2009 | Kuduvalli | A61N 5/1049 378/205 |
| 7,590,219 | B2* | 9/2009 | Maurer, Jr. | A61N 5/103 378/145 |
| 7,605,365 | B2* | 10/2009 | Chen | G01T 1/169 250/252.1 |
| 7,619,374 | B2* | 11/2009 | Aoi | A61N 5/10 315/39 |
| 7,656,998 | B2* | 2/2010 | Main | A61N 5/1049 378/19 |
| 7,693,257 | B2* | 4/2010 | Allison | A61N 5/103 378/108 |
| 7,894,649 | B2* | 2/2011 | Fu | A61N 5/1049 382/128 |
| 7,902,515 | B2* | 3/2011 | Navarro | A61N 5/1083 250/374 |
| 8,050,384 | B2* | 11/2011 | Carol | A61N 5/10 378/64 |
| 8,126,114 | B2* | 2/2012 | Naylor | A61N 5/1049 378/65 |
| 8,180,020 | B2* | 5/2012 | Kilby | A61N 5/1031 378/65 |
| 8,183,522 | B2* | 5/2012 | Celi de la Torre | G01T 1/169 250/252.1 |
| 8,303,476 | B2* | 11/2012 | Francescatti | A61N 5/1015 600/1 |
| 8,321,179 | B2* | 11/2012 | Simon | A61N 5/10 250/252.1 |
| 8,520,801 | B2* | 8/2013 | Henning | A61N 5/1083 378/65 |
| 8,559,596 | B2* | 10/2013 | Thomson | G06T 7/0014 378/65 |
| 8,559,598 | B2* | 10/2013 | Kindlein | A61N 5/1001 378/121 |
| 8,602,647 | B2* | 12/2013 | Navarro | G01T 1/02 250/252.1 |
| 8,655,429 | B2* | 2/2014 | Kuduvalli | A61N 5/1049 600/407 |
| 8,792,613 | B2* | 7/2014 | Gardner | A61B 5/04021 378/65 |
| 8,804,901 | B2* | 8/2014 | Maurer, Jr. | G06T 7/0014 378/25 |
| 8,917,813 | B2* | 12/2014 | Maurer, Jr. | A61N 5/10 378/65 |
| 8,929,511 | B2* | 1/2015 | van der Veen | A61B 6/542 378/65 |
| 8,934,605 | B2* | 1/2015 | Maurer, Jr. | A61N 5/10 378/65 |
| 8,989,846 | B2* | 3/2015 | Kuduvalli | A61B 6/00 378/181 |
| 8,995,616 | B2* | 3/2015 | van der Veen | H01J 35/32 378/65 |
| 9,036,787 | B2* | 5/2015 | de Jager | A61N 5/10 378/140 |
| 9,108,048 | B2* | 8/2015 | Maurer, Jr. | A61B 6/5247 |
| 9,168,391 | B2* | 10/2015 | Henning | A61N 5/1049 |
| 9,289,268 | B2* | 3/2016 | Ramraj | A61B 6/0457 |
| 9,561,009 | B2* | 2/2017 | Woudstra | A61N 5/10 |
| 9,616,251 | B2* | 4/2017 | Filiberti | A61N 5/1075 |
| 9,724,066 | B2* | 8/2017 | Van Der Veen | A61B 6/583 |
| 9,743,912 | B2* | 8/2017 | Fichtinger | A61B 8/587 |
| 2004/0227056 | A1 | 11/2004 | Neuberger et al. | |
| 2007/0076851 | A1 | 4/2007 | Pellegrino | |
| 2014/0121501 | A1 | 5/2014 | Fichtinger et al. | |

\* cited by examiner

ROBOTIC IORT X-RAY RADIATION SYSTEM WITH CALIBRATION WELL

CROSS-REFERENCE TO RELATED APPLICATIONS

This application claims the benefit of U.S. provisional patent application 62/551,417, filed on Aug. 29, 2017.

BACKGROUND

Statement of the Technical Field

The inventive arrangements relate to radiation therapy, and more particularly to systems and methods for intraoperative radiation therapy.

Description of the Related Art

Cancer surgery can involve removal of a cancerous tumor and some normal tissue surrounding the tumor. For example, Breast Conserving Surgery (BCS) is a type of cancer surgery in which a cancerous lump and part of the surrounding breast tissue (as opposed to the entire breast) is removed during surgery. The surgery is usually followed by a moderate-dose radiation therapy which is intended to eradicate any traces of cancerous tissue from a tumor bed (vascular and stromal tissue that surrounds a cancerous tumor). Radiotherapy techniques can involve an externally delivered radiation dose using a technique known as external beam radiotherapy (EBRT). But conventional EBRT can increase the risk of missing an intended target volume. To address this problem, intraoperative radiotherapy (IORT) is sometimes used. IORT involves the application of therapeutic levels of radiation to a tumor bed while the area is exposed and accessible during excision surgery. The benefit of IORT is that it allows a high dose of radiation to be delivered precisely to the targeted area with minimal exposure to surrounding tissues. IORT also avoids the usual delays which are associated with the time between when the surgical removal of the cancerous tissue and the EBRT.

When IORT is appropriate a surgeon will remove a cancerous tumor after which a radiation oncologist will position a radiation applicator or treatment head within the patient, in the area where the tumor was previously located. Such a treatment head can generate low energy X-Rays within the tumor cavity from which the cancerous tumor was removed.

SUMMARY OF THE INVENTION

An IORT X-ray delivery system includes a portable base unit. A first end of a robotic arm is mounted to the base unit and an X-ray treatment head is disposed on a second end of the robotic arm distal from the first end. The X-ray treatment head is comprised of at least one X-ray component configured to generate therapeutic radiation in the X-ray wavelength range. A calibration well is disposed at a predetermined location in the portable base unit. The calibration well is comprised of a recess into which the X-ray treatment head can be received. The calibration well has at least one port through which the X ray treatment head can be inserted by the robotic arm for calibration operations. The calibration well includes a plurality of X-ray radiation sensing elements (XRSE) disposed at distributed locations around a periphery of the calibration well.

The IORT X-ray delivery system also includes a control system. The control system is configured to perform at least one calibration process which involves a positioning operation in which the robotic arm is controlled by the control system to insert the X-ray treatment head through the port so that the X-ray treatment head is disposed at a predetermined calibration location inside the calibration well. The control system is further configured to control the X-ray component to produce an X-ray emission having a beam pattern, during a time when the X-ray treatment head is disposed at the predetermined calibration location. The control system is responsive to sensing data received from the XRSE, to determine at least one of a measured intensity and a measured beam pattern of X-ray radiation produced by the X-ray treatment head as a result of the X-ray emission.

The control system compares at least one of the measured intensity and the measured beam pattern, respectively to a specified intensity value and a specified beam pattern. The control system is configured to modify at least one operating parameter of the IORT X-ray delivery system responsive to the comparing. According to one aspect, the operating parameter is a duration of a treatment time during which a therapeutic dose of X-ray radiation is delivered. According to another aspect, the operating parameter is a beam control parameter which determines a pattern or shape of the beam pattern.

In other scenarios, the operating parameter can include a robotic arm control parameter. For example, such a control parameter can determine a static position of the X-ray treatment head to be used when the therapeutic dose of X-ray radiation is applied. The operating parameter can also be a motion control parameter which defines a dynamic movement of the robotic arm to be performed while the therapeutic dose of X-ray radiation is applied. In such a scenario, the dynamic movement can be a movement which minimizes variations in X-ray dose delivered by the treatment head to surfaces of a tumor bed.

The solution also concerns a method for calibrating an IORT X-ray delivery system. The method can involve supporting a first end of a robotic arm on a portable base unit and supporting on a second end of the robotic arm an X-ray treatment head, where the X-ray treatment head includes at least one X-ray component configured to generate therapeutic radiation in the X-ray wavelength range. A control system causes the robotic arm to insert the X-ray treatment head in a calibration well that is defined by a recess provided at a predetermined location in the portable base unit. The control system will then activate the X-ray component to generate an X-ray emission from the X-ray treatment head while the X-ray treatment head is disposed at a predetermined calibration location in the calibration well. Thereafter, the control system can receive sensor data from a plurality of X-ray radiation sensing elements (XRSE) disposed at distributed locations around a periphery of the calibration well. The sensor data is used to determine at least one of an intensity and a beam pattern of X-ray radiation produced by the X-ray treatment head.

In some scenarios, the control system automatically compares at least one of the measured intensity and the measured beam pattern, respectively to a specified intensity value and a specified beam pattern. Thereafter, the control system can be operated so as to automatically modify at least one operating parameter of the IORT X-ray delivery system responsive to the comparing. For example, the operating parameter can include a duration of a treatment time during which a therapeutic dose of X-ray radiation is delivered. The operating parameter can also include a beam control parameter which determines a pattern or shape of the beam pattern.

In other scenarios, the operating parameter can include a robotic arm control parameter which determines a static position of the X-ray treatment head to be used when the therapeutic dose of X-ray radiation is applied. Alternatively, the operating parameter can be chosen to comprise a motion control parameter. For example, the motion control parameter can defines a dynamic movement of the robotic arm to be performed while the therapeutic dose of X-ray radiation is applied. In some scenarios, the dynamic movement can be chosen so as to minimize variations in X-ray dose delivered by the treatment head to surfaces of a tumor bed.

BRIEF DESCRIPTION OF THE DRAWINGS

The disclosure herein will be with reference to the following drawing figures, in which like numerals represent like items throughout the figures, and in which.

DETAILED DESCRIPTION

Figure 1:
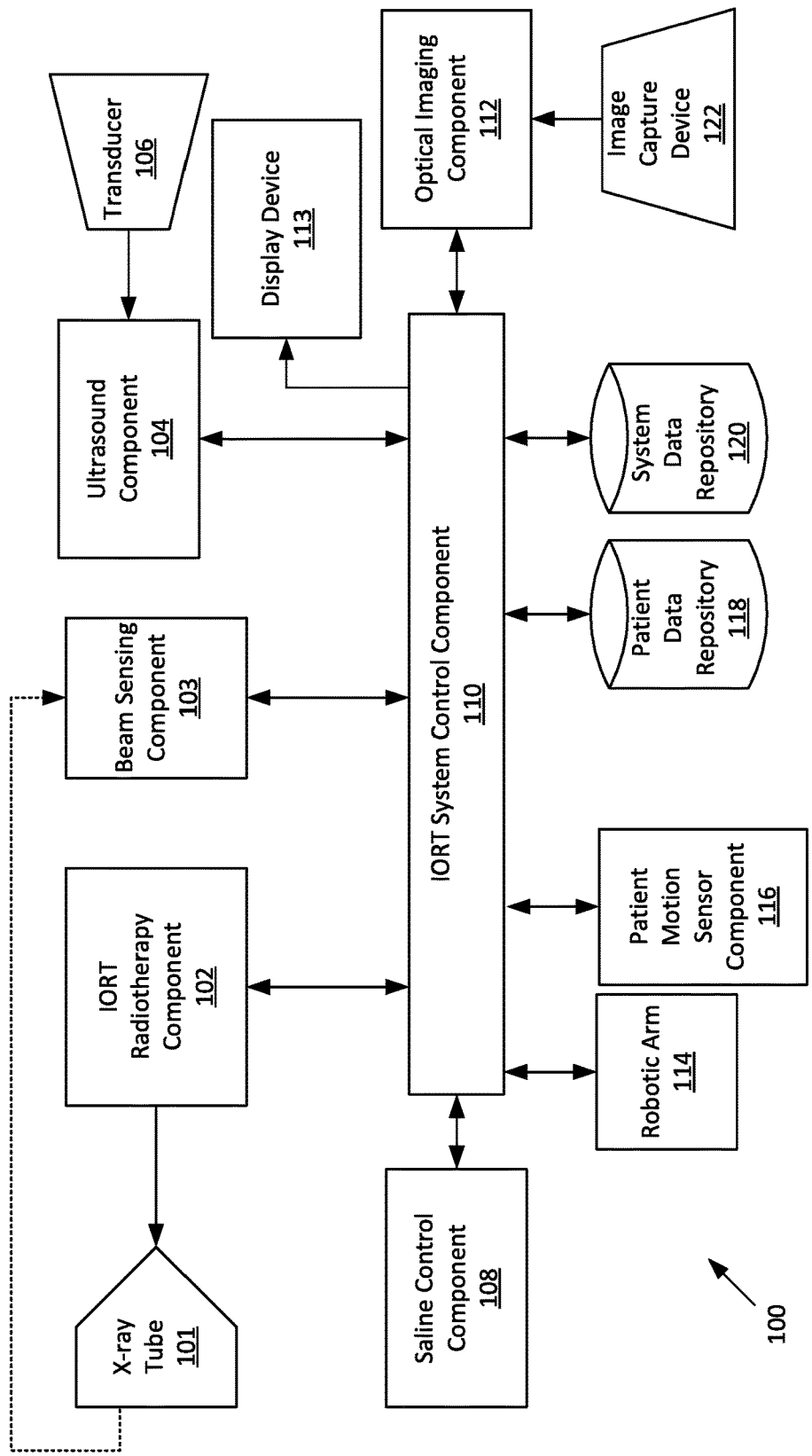
FIG. 1 is a block diagram that is useful for understanding a robotic IORT system.

It will be readily understood that the components of the systems and methods described herein could be arranged and designed in a wide variety of different configurations. Thus, the following more detailed description, as represented in the figures, is not intended to limit the scope of the present disclosure, but is merely representative of certain exemplary scenarios which are useful for understanding the disclosure. While the various aspects are presented in drawings, the drawings are not necessarily drawn to scale unless specifically indicated.

A robotic IORT system as disclosed herein comprises an X-ray generating system, and includes a X-ray treatment head which is secured to a movable end portion of a robotic arm. X-ray energy is emanated or radiated from the treatment head when the X-ray generating system is activated. In some scenarios, the X-ray treatment head can be disposed at the tip end of an elongated applicator body which is secured to the robotic arm by a base portion. By controlling the position of one or more robotic arm joints, the robotic arm can maintain the treatment head in a fixed position within or outside of the patient for application of X-ray therapy. For example, the robotic arm can control a position of the X-ray treatment head for interventions relating to IORT. In some scenarios, the movement of the robotic arm can be synchronized with the breathing movements of the patient so that the treatment head always has the same relative position to the tissue comprising the tumor bed. The robotic arm supports the X-ray treatment head and can provide some or all of the necessary utility channels to support IORT functions and operations. For example, the robotic arm can provide one or more liquid conduits to facilitate delivery of saline to an inflatable balloon and for draining saline from the balloon.

The above-described system can be used with any source of X-ray radiation now known, or known in the future, provided that the treatment head from which X-ray energy is radiated can be supported and maintained in a desired position by the robotic arm. For example, a miniaturized X-ray source could be disposed in the treatment head that is supported the robotic arm. However, one advantage of the foregoing arrangement is that it facilitates the use of a relatively larger sized X-ray generating system for IORT in place of a miniaturized X-ray source. An example of such a larger X-ray generating system is disclosed in U.S. patent application Ser. No. 15/941,547, filed Mar. 30, 2018, entitled Three-Dimensional Beam Forming X-ray Source, the entirety of which is incorporated herein by reference. The larger sized X-ray generating system can provide all of the benefit of a miniature X-ray source but without the added cost associated with the miniature X-ray source. The functional result for the patient is the same as with the miniature X-ray source disposed in a flexible catheter. The X-ray source in both scenarios will move with body tissue movement. But the durability and lower cost of the larger X-ray generating system will greatly reduce the overall cost of IORT treatment.

The X-ray generating system as described here can also include a balloon disposed over the treatment head which is inserted into the tumor cavity. The balloon can be inflated or deflated by controlling a flow of saline to the interior cavity of the balloon. An inflatable balloon disposed around the X-ray treatment head can help ensure that a homogeneous radiation dose is applied to all portions of the tumor bed. One aspect of the balloon concept is that, when properly inflated, it urges all of the tissues comprising the tumor bed to conform to a roughly spherical shape as defined by the inflated balloon. Consequently, a radiation source disposed in the center of the balloon will be approximately equidistant from all of the tissue surfaces which define the tumor bed. If the treatment head produces an approximately spherical or isotropic radiation pattern, then the result will be a substantially homogeneous radiation dose being applied to all portions of the tumor bed.

In an IORT system as described herein, the amount of X-ray radiation that is applied to various portions of the tumor bed by an X-ray source must be carefully controlled. But the X-ray generating system, because of its design, a malfunction, and/or functional degradation over time, may not produce an expected X-ray radiation pattern and/or intensity. Such a scenario can lead to different portions of the tumor bed receiving levels of X-ray radiation which are inconsistent or otherwise not intended.

Further, recent developments with X-ray sources have the potential to facilitate X-ray beam steering and beam shaping within the tumor cavity. Collectively, this capability is sometimes referred to herein as beam sculpting. For example, an X-ray generating system with beam sculpting capability is disclosed in U.S. patent application Ser. No. 15/941,547, filed Mar. 30, 2018, entitled Three-Dimensional Beam Forming X-ray Source. Although such beam sculpting capability offers many advantages in an IORT scenario as described herein, it also creates certain treatment challenges, because a treatment specialist must be certain that the sculpted shape of the beam that is actually produced is well defined during IORT. In this regard, there is currently no good method to verify that a beam steering or beam sculpting operation has occurred properly and/or is delivering a desired amount of X-ray radiation to a particular portion of a tumor bed.

Accordingly, the present solution involves a system for calibrating an X-ray source for IORT. The calibration system can ensure that the X-ray beam that is produced is properly sculpted so as to be consistent with a treatment plan. The calibration system can also provide a basis for an IORT treatment plan to be modified. For example, such modifications may involve comparing a beam shape, direction, and intensity of a beam measured by the calibration system, to an X-ray beam that is specified by a particular treatment plan. Based on such a comparison, adjustments can be made to beam sculpting control parameters so that the sculpted X-ray beam actually produced is more closely conformed with an X-ray beam specified by a treatment plan. In other scenarios, the treatment plan can be modified to accommodate limitations or variations in the X-ray beam that is actually produced. For example, this can be accomplished by adjusting a position of a treatment head, an orientation of a treatment head, and a duration of time in which the tissue is exposed to the X-ray beam.

In some scenarios, the adjusted or modified position of the treatment head can be a static position in which the treatment head does not move during a time when radiation treatment is being applied. However, the robotic arm can also facilitate a predetermined motion or movement of the treatment head during a IORT session to ensure that all portions of a tumor bed receive a predetermined amount of radiation in accordance with a treatment plan. In some scenarios, the movement can occur concurrent with the application of the X-ray radiation. In other scenarios, the application of X-ray radiation can be temporarily interrupted while the robotic arm repositions the treatment head. In some scenarios, these techniques can be applied to help minimize variations in X-ray dose delivered by the treatment head to surfaces of a tumor bed. For example, such an approach can be advantageous when limitations with respect to the beam steering are such that beam uniformity, shape or direction prevent a desired beam from being achieved.

The IORT system solution can comprise a portable base unit or cart (e.g. a movable cart on casters) to which a robotic arm is attached. An X-ray generating system can include a treatment head which is fixed to a first end of the robotic arm distal from a second end of the robotic arm which is attached to the portable base unit. A power supply and control unit for the IORT system (including the robotic arm) can be integrated within the base unit.

The solution disclosed herein further involves the use of a calibration well, which is included as part of the base unit that supports the robotic arm. The calibration well is advantageously mounted in or on the base unit so it has a fixed position relative to the robotic arm. Accordingly, the position of the well is always known by a robotic arm control unit. The position of the well is selected so that the robotic arm, when commanded to do so, can move the X-ray treatment head to a position within the calibration well. Within the calibration well, a plurality of X-ray radiation sensor elements (XRSE) are disposed to measure an X-ray beam intensity and/or pattern. The sensors can be disposed to line the interior walls which define the well. One or more different types of sensors can be provided for this purposes (e.g. absolute beam intensity vs. pattern measurements). Position sensing elements can be provided inside the well to verify a presence and/or position of an X-ray treatment head when it has been moved into position within the well.

When the output of the X-ray treatment head is to be evaluated (e.g., pattern and/or field strength), the robotic arm is controlled by the control unit to move the X-ray treatment head into a predetermined position in the well. For purposes of this disclosure, an X-ray treatment head can be understood to be a portion of the X-ray generating system from which X-ray radiation is actually emanated for therapeutic treatment purposes. Since the well is mounted in a fixed position directly in or on the base unit of the X-ray system, the control unit will know an exact position where the X-ray treatment head must be positioned for evaluation purposes. The joint positions of the robotic arm are always known to the robotic arm control system. The robotic arm is mounted in a fixed location relative to the base unit. Accordingly, the precise robotic arm joint positions required to position the treatment head within the well will be known to the robotic control system. So one advantage of including the calibration well as part of the IORT system base unit is that the sculpted beam pattern which is detected can be known and registered relative to the position and orientation of the robotic arm. After the treatment head is removed from the calibration well, the relative position and orientation of the treatment head are always known as a function of the robotic arm joint positions. Accordingly, the exact position and orientation of the radiation pattern can also be known. This information can be useful for purposes of ensuring that the correct amounts of X-ray radiation are directed to different locations within a tumor cavity when performing an IORT intervention as described herein. The detected beam pattern can also be used as a basis for adjusting beam control parameters to vary a direction, shape and/or intensity of the beam. These beam control parameters will naturally vary in accordance with the particular type of X-ray source which is being employed in a particular scenario. The detected beam pattern can also be used as a basis to modify a treatment plan. Such modifications can involve changing a static position of a treatment head within a wound cavity during application of radiation therapy, and/or dynamically varying a position of the treatment head over a duration of an IORT session. These modifications can also involve varying an orientation of the treatment head over a duration of an IORT session.

The XRSE disposed within the well are advantageously arranged at a plurality of predetermined locations. For example, in some scenarios, these locations can be known with respect to each of a plurality of orthogonal axis which define an x, y and z coordinate system. When calibration operations are to be performed, the position of the X-ray treatment head can be controlled by means of the robotic arm so that the treatment head is disposed precisely at the origin of the coordinate system. In other scenarios, the origin of the x, y, and z coordinate system can be determined dynamically in accordance with the position of the treatment head. In either scenario, a plurality of XRSE can be aligned with a plurality of points within the well which define a grid lining the interior of the cavity. In some scenarios, the entire cavity can be lined with XRSE. However, the solution is not limited in this regard and in other scenarios, only a portion of the entire cavity can be lined with the XRSE. Still, it is advantageous that a sufficient number of XRSE are disposed so as to detect X-ray radiation in a plurality of different directions which surround the X-ray treatment head.

The XRSE will communicate the result of their sensing activities to a control system, which monitors the X-ray radiation dose detected by each of the sensors. Each XRSE will have a known location on the surface of the cavity, and this location will be known to the control system. Consequently, the control system can determine the exact dose of X-ray applied in radial directions extending from the X-ray treatment head. By comparing the relative intensity measured by the various XRSE, a beam pattern produced by the X-ray treatment head can be determined. These results can be displayed to a treatment specialist on a computer display. The treatment specialist can thereby observe any variations in the actual amount of X-ray radiation applied by an X-ray source relative to an expected beam pattern. For example, this can be accomplished by comparing the measured beam pattern to an expected beam pattern.

In some scenarios, the measured X-ray radiation pattern can be used as a basis to control the X-ray generating system so that an actual beam pattern that is produced by the treatment head will match a desired beam pattern. For example, this could be accomplished by adjusting at least one characteristic or control function of the X-ray generating system to modify the X-ray beam that is produced. The detected radiation pattern and intensity levels detected when the treatment head is in the calibration well can also be used by the treatment specialist to help position the X-ray treatment head. For example, in some scenarios, the treatment specialist can adjust the position of a treatment head containing an X-ray source so that minimum or maximum of an X-ray radiation pattern is directed toward a particular location. Alternatively, the treatment head can be positioned to facilitate greater uniformity in X-ray intensity within the tumor cavity. This could be accomplished by periodically varying a position of the treatment head to account for various minima and maxima associated with the beam. These adjustments can be performed in any suitable manner consistent with the operation of a particular X-ray generating system in use. As such, it is contemplated that beam adjustments could be implemented manually, electro-mechanically, electronically, or by means of repositioning a robotic arm.

The various aspects of the present disclosure will be described with respect to the attached drawings of an exemplary system that can deliver both therapeutic IORT functionalities through a single platform to better serve and benefit the practitioner and patient. The exemplary system can include multiple imaging devices and a radiotherapy device used cooperatively to perform IORT in accordance with the present disclosure. In some scenarios, the system can involve use of a robotic IORT system.

As explained below in further detail, the robotic IORT system can use a robotic arm to help ensure a consistent position of an X-ray treatment head during IORT. The robotic arm can facilitate controlled movement of the X-ray treatment head disposed within the patient in response to autonomic motions of the patient associated with breathing and the like. Such motion control can be facilitated by use of force sensors disposed in the robotic arm, or by means of fiducial markers disposed on the patient to track such movements. These and other features of the present solution will become apparent from the description below.

Referring now to FIG. 1 there is shown a high level block diagram representation of a robotic IORT system 100 which is useful for understanding the invention. The exemplary system 100 can include an X-ray generating system comprised of a radiotherapy component 102 with X-ray tube 101. The system will also include an optional ultrasound component 104 with a transducer 106, an optical imaging (OI) component 112 with an associated image capture device (ICD) 122. The system also includes a robotic arm 114, optional patient motion sensor 116, and an optional saline control component 108. In some scenarios described herein, the system control component 110 guides the robotic arm 114 during IORT operations. Such guidance can in some scenarios be based on images and data obtained from one or more of a patient motion sensor component 116, the ultrasound component 104, transducer 106, OI component 112, and ICD 122. X-ray energy produced by the X-ray tube 101 can be applied to a patient using an X-ray applicator or treatment head (not shown in FIG. 1), which is fixed to a movable end of the robotic arm.

The saline control component 108 can comprise a pump and one or more selectively controlled valves, all under the control of software and hardware elements associated with the system control component. The pump can be connected to a reservoir or source of saline solution. As such, the saline control component can control a flow of saline to and from a balloon (not shown in FIG. 1) that is disposed over an X-ray treatment head. When IORT operations are to be performed, the treatment head (enclosed by the balloon) is inserted into a cavity from which a cancerous tumor has been removed. The balloon is then inflated with saline. Once inflated, the X-ray tube 101 and radiotherapy component 102 are used to apply radiation to the walls of the cavity formed by the tumor bed. During the application of radiation, the saline control component can monitor and maintain fluid circulation and pressure within the balloon. After IORT treatment has been completed, the saline control component 108 releases the saline to deflate the balloon, after which the X-ray treatment head (along with the balloon) is withdrawn from the cavity.

The robotic arm 114 is advantageously selected to be a robotic system that provides freedom of movement about multiple orthogonal axes (e.g. up to seven axes) and includes lightweight force and torque sensors (not shown in FIG. 1) to ensure safe operation with humans without the need for a safety fence. Exemplary robots of this kind are commercially available from various sources. For example, KUKA Roboter GmbH of Augsburg Germany (KUKA) manufactures a line of direct human-robot collaboration (HRC) capable lightweight robots which are suitable for direct human-robot interaction. These robots include the LBR iiwa model and/or the LBR iisy model produced by KUKA. Robots of this kind are well suited for the delicate operations described herein because they include high-grade joint torque sensors included in all six axes, which can detect the slightest of external forces resulting from contact with objects, and can respond by immediately reducing a level of force and speed associated with robot movements.

If a patient motion sensing component 116 is provided, it can include optical sensors, ultrasound sensors, pressure sensors, laser sensors or any other type of sensor which is useful for monitoring movement of a patient undergoing IORT treatment. For example, such movement may comprise respiratory movement and/or digestive system movement which occurs during IORT. The patient motion sensor component can be separate from the robotic arm 114 and/or may be integrated into the robotic arm to facilitate such sensing. In some scenarios, data from ultrasound component 104, transducer 106, optical imaging component 112, and image capture device 122 can be used for patient motion sensing as described herein. The information from these sensors can be used instead of or in conjunction with sensing data acquired from patient motion sensor component 116.

In a scenario where system control component 110 receives patient motion sensor data, such information can be used to control the robotic arm 114. For example, during IORT operations as described herein, a motion of the robotic arm can be controlled in accordance with the patient motion sensing data to ensure that the X-ray treatment head moves in sync with the tissue natural movement. Such natural tissue movement may be due to respiratory or other body functions. Thus, the robotic arm will precisely maintain a position of the X-ray treatment head relative to the tumor bed which is receiving radiation therapy. The precise control over the motion and position of the X-ray treatment head can help ensure that all areas of the tumor bed receive a homogenous exposure to the applied radiation. In order to accomplish this result, the robotic arm can move along multiple motion axes (e.g., up to seven motion axes) to maintain a relative position of the X-ray treatment head within the cavity from which the cancerous tumor was removed.

The IORT radiotherapy component 102 can be comprised of X-ray tube driver circuitry, high-voltage power supplies, control circuits and other components which are needed to cause an X-ray tube 101 to generate X-ray radiation as described herein. In some scenarios, portions of the IORT radiotherapy component 102 can be disposed in a head unit which is fixed at a movable end of the robotic arm. In some scenarios, the X-ray tube 101 may also be disposed at a movable end of the robotic arm. The radiotherapy component 102 can be configured to facilitate treatment of a tumor bed in accordance with IORT treatment methods which are now known or known in the future. In some scenarios, the X-ray tube 101 is advantageously configured to facilitate an isotropic source for x-ray photon particles to perform IORT of a tumor bed. In other scenarios, the X-ray tube 101 can be configured to facilitate a directional X-ray beam.

In some scenarios, the X-ray tube can be advantageously selected and purposely designed so that it has a relatively small size such that it fits within a cavity from which a cancerous tumor has been removed, yet it is robust and large enough to withstand numerous treatment sessions without burning out, or failing. Any suitable X-ray source can be used provided that it satisfies these known requirements of an IORT X-Ray source. An example of a commercially available source of this kind is the Axxent® Electronic Brachytherapy system which is available from Xoft, Inc. of San Jose, Calif. Another X-ray source that is suitable is described in U.S. patent application Ser. No. 15/941,547, filed Mar. 30, 2018, entitled Three-Dimensional Beam Forming X-ray Source, the disclosure of which is incorporated herein by reference.

The radiotherapy component 102, which can be a superficial radiotherapy component, and X-ray tube 101, can together include control circuitry, one or more cooling elements for the X-ray tube, power supplies, one or more high voltage generator, one or more interchangeable applicators, and one or more hardware timers that work in concert with a software timer for redundancy and other purposes. It is contemplated that the X-ray tube utilized herein will be selected so that is optimized for IORT interaction with tumor bed tissue, and has minimal effects at deeper tissue depths. For example, a conventional superficial radiation therapy (SRT) type of X-ray unit can be used for this purpose. As will be appreciated, an SRT type of X-ray unit produces low energy X-rays that is suitable for this purpose.

In some scenarios, a solid-state X-ray beam sensing component 103 can monitor the beam output of the radiotherapy component 102 and x-ray tube 101, along with overall system stability and yield. The solid-state X-ray beam sensing component 103 can include one or more XRSE which are mounted within a X-ray calibration well. As such, the performance of the X-ray generating system can be evaluated by moving the treatment head into the calibration well. These calibration operations can be performed whenever the system 150 needs to be tested for quality control, or overall system 150 diagnosis purposes. However, it can be advantageous to perform such calibration operations immediately before beginning an IORT procedure so that a precise and up-to-date characterization can be determined for the operations of the X-ray tube 101 and the X-ray beam.

The present disclosure contemplates that in addition to or as an alternative to using a X-ray based radiotherapy in system 100, any other types of radiotherapy can be used in system 100. Thus, the components for radiotherapy can be selected to support photon-based radiotherapy (e.g., x-rays and gamma rays), particle-based radiotherapy (e.g., electrons, protons, neutrons, carbon ions, alpha particles, and beta particles), or any combinations thereof which may be determined to be suitable for IORT now or in the future.

If an ultrasound component 104 is provided, it can include control circuitry, system drivers, operation control software, and a transducer 104, which can be high frequency ultrasonic transducer, for tissue imaging of the tumor bed. The ultrasound component 104 communicates with the software of the system control component 110 via a bus and system drivers. The ultrasound component 104 and transducer 106 are provided in exemplary system 100 to provide structural or anatomical data associated with the tumor bed without exposing a subject to ionizing radiation. However, the present disclosure contemplates that ultrasound component 104 and transducer 106 can be replaced or supplemented in system 100 with components for supporting any other types of imaging techniques that also do not utilize ionizing radiation. For example, optical coherence tomography or laser range scanning (LIDAR), to name a few.

The ultrasound component 104 can be any ultrasound device capable of operating within an acceptable bandwidth. For example, the ultrasound component and transducer 106 can operate in a bandwidth of approximately 2 MHz to approximately 70 MHz, and may be implemented with an electro-mechanical, or a solid state transducer. The system 100 can provide the ultrasound component 104 at least partially integrated inside a system 100 housing coupled to a data bus, with a transducer head 106 outside of the housing as discussed in relation to FIGS. 2 and 3. The ultrasound component 104 and other components of the system 100, can be in communication with a data bus to facilitate communication of image data to system control component 110 and/or display device 113. A suitable interface standard can be used for this purpose such as peripheral component interconnect (PCI/PCIe), universal serial bus (USB/USBII/USBIII/USB-C), Ethernet, or Firewire. However, the present disclosure contemplates that any other interface and/or communications standards can be used.

The optical imaging component 112 can include control circuitry, system drivers, operation control software, and one or more image capture devices 122, for imaging a tumor bed. According to one aspect, the optical imaging component is a spectroscopic imaging device. For example, the optical imaging component can comprise a multispectral imaging device that captures image data at a plurality of optical frequencies. Such multispectral imaging component can be configured to utilize optical energy from the visible portion of the light spectrum for imaging purposes, but can also utilize optical energy from frequencies beyond the visible light range (e.g. infrared and near ultraviolet). Alternatively, the optical imaging component can comprise a hyperspectral imaging device wherein optical information is captured from across the electromagnetic spectrum at each pixel in the captured image. As a further alternative, the spectroscopic imaging device can be configured for Raman spectroscopy which captures changes in the frequency of photons in monochromatic light which result from interaction with tissue within the tumor bed. As a further alternative, the spectroscopic imaging device can be configured for photoacoustic imaging, which utilizes non-ionizing laser pulses or an alternative light source to image the residual cavity tissue.

The optical imaging component 112 communicates with the software of the system control component 110 via a bus and system drivers. The present disclosure contemplates that optical imaging component 112 and the image capture device 122 can be replaced or supplemented in system 100 with components for supporting any other types of imaging techniques for extracting molecular or functional information from tumor bed tissues. For example, biomarkers can be used to enhance the usefulness of the optical imaging methods described herein. As is known, a biomarker can involve a substance which is introduced to a tissue to facilitate the identification of a disease condition such as cancer. According to one aspect, a biomarker can include any substance introduced to a tumor bed tissue which can be used to induce visually or optically detectable changes that can facilitate identification of cancerous cells. Any biomarker now known or known in the future can be used in conjunction with the optical imaging component 112 and the one or more image capture devices 122 provided that it can help facilitate identification of functional data pertaining to tumor bed tissue under observation.

Figure 2:
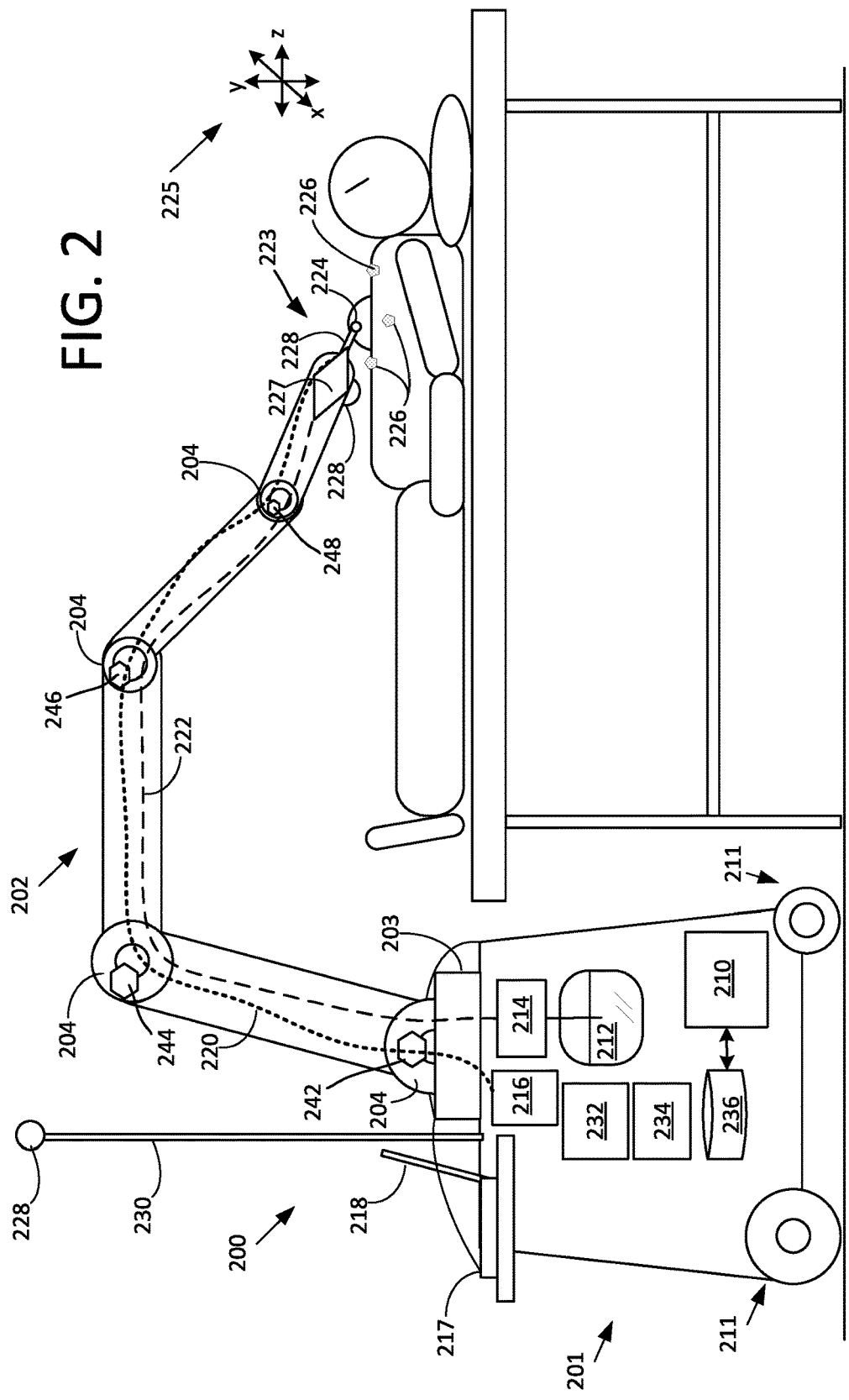
FIG. 2 is a diagram that is useful for understanding an implementation of a robotic IORT using a robotic arm and a treatment head.
Figure 3:
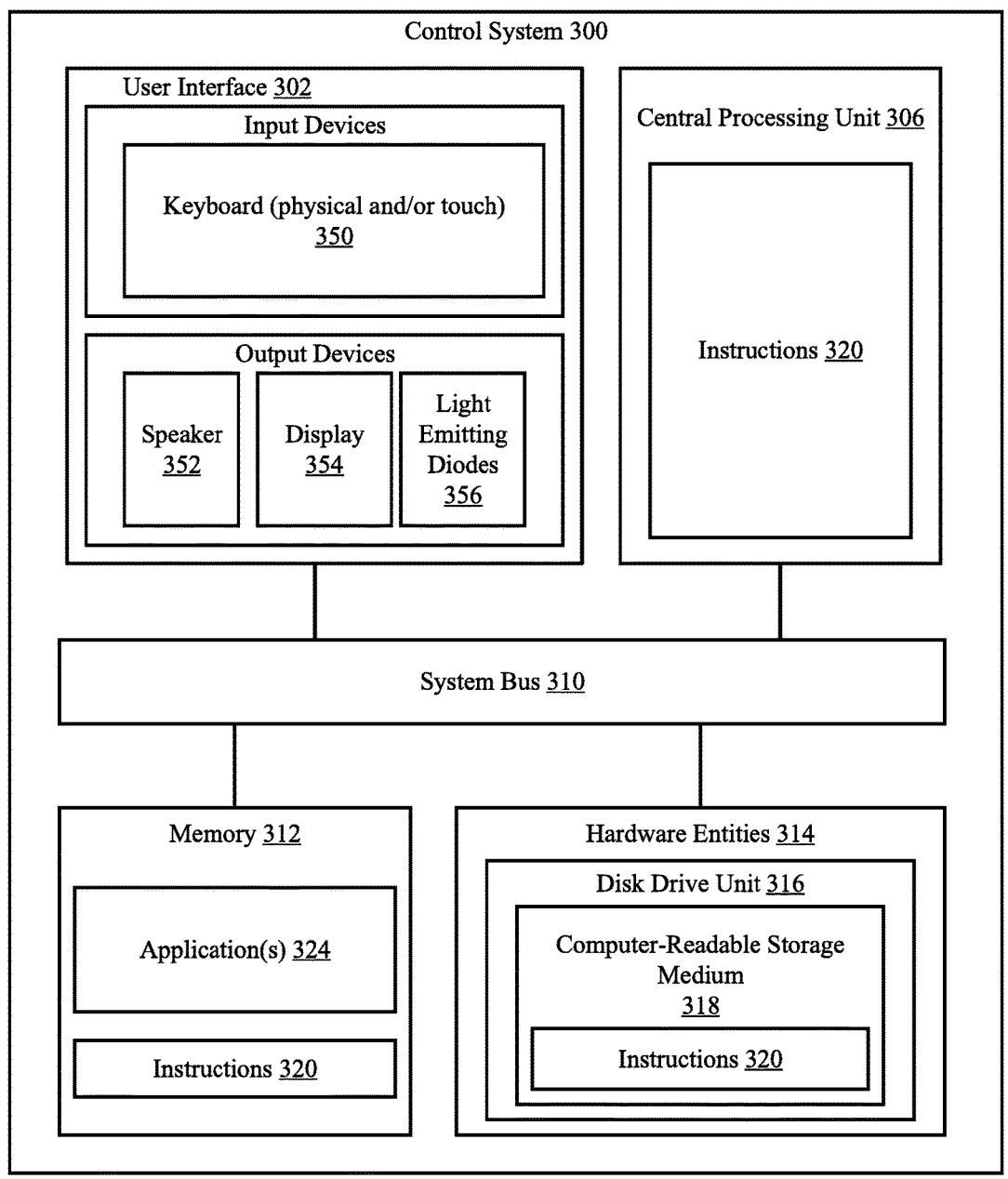
FIG. 3 is a block diagram that is useful for understanding a control system which can be used for facilitating robotic IORT as described herein.

The optical imaging component 112 can be provided at least partially integrated inside a housing of system 100 coupled to a data bus with one or more image capture devices 122 located outside of the housing as shown in FIGS. 2 and 3. The optical image component 112 and other components of the system 100 can be in communication with the data bus and the respective other components of the system 100 utilizing interface standards such as peripheral component interconnect (PCI/PCIe), universal serial bus (USB/USBII/USBIII/USB-C), Ethernet, or Firewire, to name a few. However, the present disclosure contemplates that any other interface and/or communications standards can be used.

In some scenarios, the system 100 utilizes the ultrasound component 104 with a transducer 106 to scan and image a tumor bed, to obtain structural or anatomical information about the region of interest. The system can also utilize the optical imaging component 112 with image capture device 122 to optically scan and image the same volume to obtain functional and/or metabolic information pertaining to the skin tissue or portions thereof. As used herein, the functional and/or metabolic information referenced herein can include any information pertaining to the biological function, behavior or processes at work in a particular cell or group of cells. The ultrasound and optical scanning processes will be described below in further detail. A registration process can be used to facilitate alignment of the image data acquired using the ultrasound and optical scanning methods. After the region of interest has been scanned and imaged by the system 100, the image data is processed by the system's software. The image data acquired using the ultrasound and optical scanning methods can be registered and then fused or merged to form a single image. In the fused image, the image data acquired by using ultrasound is basically superimposed over the image data acquired by using the optical scanning method described herein. The result is a hybrid image which includes detailed anatomical and/or structural data for the tumor bed with the functional data for the same tissue volume superimposed. This process can be used after tumor excision to help identify any portions of the tumor bed that may comprise cancerous tissue.

The system 100 is controlled and operated by the system control component 110, which can include a central computer with a motherboard that runs operation and control software with various parallel and connected boards that allow it to control, communicate, and monitor the various sub-components and modules of the system 100. This achieves harmonious functionality between the three main clinical components of the system 100 including the radiotherapy component 102, the robotic arm 114 and the patient motion sensing component. The system control component 110 can be communicatively connected with data repositories, including a patient data repository 118 and a system data repository 120.

The software or instructions executed by the system control component can control the system 100 functions, verify the safety mechanisms, and the service and calibration functions. The control system component 110 can be in communication with a machine-readable medium which can be static memory on which is stored one or more sets of instructions (e.g., software) embodying any one or more of the methodologies or functions described herein, including those methods illustrated herein. The instructions may also reside, completely or at least partially, within the system data repository, static memory, or within the processor, or a combination thereof, during execution thereof by the system 100. The system data repository and patient data repository and the processor also may constitute machine-readable media.

The patient data repository 118 and the system data repository 120 can be a solid-state drive, hard drive or other memory device. The patient data repository 118 can store patient-related data and treatment parameters, such as patient records, treatment session details, and disease documentation and photos. The system data repository 120 stores all system-related data and parameters, such as the system log, x-ray calibration data, and system diagnostics results. The patient data repository 118 and the system data repository 120 can be discrete devices or physically combined. One or more partitions can be used if the repositories 118 and 120 are combined, such as a single repository. Both data repositories will be mirrored and backed up to a secured and encrypted HIPAA-compliant cloud storage medium.

One example of a robotic IORT system 200 is shown in FIG. 2. The system 200 can include a base unit 201 with various components mounted thereon or connected therewith. These components can include a robotic arm 202, an X-ray generating system, a saline reservoir 212, a saline control element 214, and a system control component 210. The X-ray generating system is comprised of an IORT radiotherapy component, which in some scenarios can be distributed between a base unit portion 216 and a head unit portion 223. The base unit can also include an optical imaging component 232, an ultrasound component 234, and a data storage device 236 for storing patient and/or system data. The base unit 201 is advantageously a compact unit such as one with a 30" x 30" footprint and can be mounted on casters 211 for ease of maneuverability. The base unit 201 can include a power lead for optionally providing power to all of the components housed in or connected to the base unit 201. In this regard, the base unit 201 can contain one or more computers 217 for controlling the system 200 and/or analyzing and processing data obtained from the system 200 components. In some scenarios, a monitor 218 can be mounted to the base unit 201 to facilitate a user interface. Likewise, a terminal or an input device such as a keyboard or mouse, can be included.

A mount 203 is provided on the base unit 201 for mounting the robotic arm 202 in a fixed location on the base unit. The robotic arm 202 can have attached thereto a head unit portion 223 of the IORT radiotherapy component. An elongated applicator body 228 extends from the head unit portion 223 to a treatment head 224. The robotic arm 202 is articulated with appropriate robotic joints or articulation members 204 under the control of the system control component 210. Although not shown in FIG. 2, more or fewer articulation members 204 can be provided at different points of robotic arm 202. Such articulation members 204 can increase or decrease a number of degrees of freedom 225 of placing, orienting and moving the X-ray treatment head 224. Moreover, the number of articulation members illustrated in FIG. 2 is solely for ease of illustration. The present disclosure contemplates that the any number of articulation points can be provided so as to provide any number of degrees of freedom in robotic arm 202 as may be required for dynamically positioning and orienting the X-ray treatment head 224 with respect to the patient and/or calibration well. In some scenarios a saline conduit 222 can facilitate communication of saline from the reservoir 212 and saline control component 214 to the X-ray generating system. Similarly, one or more power and/or control signals conduit 220 can be provided. The power and/or control signal conduit can facilitate communication of power and/or control signals between the base unit portion 216 and the head unit portion 223 of the IORT radiotherapy component. These signals can be used to control and facilitate operation of the X-ray tube (not shown in FIG. 2). In some scenarios, high voltage cables, fluid conduits, and control circuitry may not be included as part of the robotic arm, but comprise a separate control cable bundle which simply attaches to the X-ray treatment head.

The patient motion sensing and tracking described herein is advantageously implemented through the integration of physical sensing means, optical sensing means or both. A main body 227 comprising head unit portion 223 can be directly mounted on or attached to the robotic arm 202. Consequently, when the patient tissue movement produces a force which is exerted on the treatment head 224, such force will be communicated through the elongated applicator body 228 and main body 227, to the robotic arm 202. This force can be the result of direct miniscule physical pressure that is exerted upon the treatment head 224 and coupled through the head unit 223 to the robotic arm. These forces can be defined by associated force vectors aligned with orthogonal x, y and z coordinate axes. The force sensing can be facilitated by physical sensors 242, 244, 246, 248 located in any of several positions throughout the robotic arm. For example, in some scenarios, the physical sensors can be comprise torque sensors associated with each of a plurality of robot arm joints 204. The physical sensors can be a combination of one or more various types, such as piezoelectric, gyroscopic, solid state, and other mechanisms and materials.

To facilitate tracking of patient motion, one or more fiducial markers 226 can be optionally be placed on portions of a patient's body. In some scenarios, the fiducial markers can comprise an optical type of fiducial markers that facilitate optical tracking of position associated with the fiducial marker. The motion of the fiducial markers can be monitored by sensors 228. The sensors 228 may be disposed on a portion of the robotic arm 202 or on a sensor supporting structure 230 which provides good visibility of the patient upon whom IORT is to be performed. The sensors 228 can comprise any type of sensor suitable for monitoring patient motion. For example, in the case where the fiducial markers are of an optical type, LIDAR methods can be used to precisely detect the location of each fiducial marker. Of course, embodiments are not limited in this regard and any other suitable type fiducial marker and associated sensing system can be used. The sensor outputs are monitored by the system control component 210 and processed by one or more motion analyzing software components (tracking system software).

The tracking system software will be periodically provided with updated data from the physical sensor information received from physical sensors 242, 244, 246, 248. Concurrently, the tracking system software is also advantageously provided with fiducial marker position information generated from one or more sensor(s) 228. The tracking system software will use the received information to generate an immediate correcting x, y, z coordinate update command for the robotic arm which reflects the subtle movement of the patient tissue. The robotic arm, subsequently, shall move to the new synchronized x, y, z coordinate/location to correspond with the patient's tissue motion. This motion correction mechanism will advantageously run in a perpetual cyclical loop to constantly sense and follow the patient tissue motion generated by respiratory or other bodily functions.

Based on analysis of forces applied to the robotic arm, and information from the physical sensors 242, 244, 246, 248, the system control component 210 controls the robotic arm 202 to ensure that the treatment head 224 is moving in precise synchronization with the patient movement. For example, the treatment head 224 can rise and fall with the respiratory action of the patient.

Referring now to FIG. 3, there is provided an illustration of an exemplary control system 300 which can be used for controlling a robotic IORT system as described herein. The control system can include, but is not limited to, machines (or computing devices) running a Windows OS (e.g., a personal computer or server). Such machines (or computing devices) are well known in the art, and will not be described in detail herein. Still, it should be understood that such machines are modified to implement all or a portion of the methods described herein. Such modifications can include software modifications, hardware modification or a combination of both.

Control system 300 may include more or less components than those shown in FIG. 3. However, the components shown are sufficient to disclose an illustrative embodiment implementing the present solution. The hardware architecture of FIG. 3 represents one embodiment of a representative control system or computing device configured to facilitate the IORT tracking control, and X-ray source calibration operations described herein.

Some or all the components of the control system 300 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 3, the control system 300 comprises a user interface 302, a Central Processing Unit ("CPU") 306, a system bus 310, a memory 312 connected to and accessible by other portions of computing device 300 through system bus 310, and hardware entities 314 connected to system bus 310. The user interface can include input devices and output devices, which facilitate user-software interactions for controlling operations of the computing device 300. The input devices include, but are not limited, a physical and/or touch keyboard 350. The input devices can be connected to the computing device 300 via a wired or wireless connection (e.g., a Bluetooth® connection). The output devices include, but are not limited to, a speaker 352, a display 354, and/or light emitting diodes 356.

At least some of the hardware entities 314 perform actions involving access to and use of memory 312, which can be a Radom Access Memory ("RAM"), a disk drive and/or a Compact Disc Read Only Memory ("CD-ROM"). Hardware entities 314 can include a disk drive unit 316 comprising a computer-readable storage medium 318 on which is stored one or more sets of instructions 320 (e.g., software code) configured to implement one or more of the methodologies, procedures, or functions described herein. The instructions 320 can also reside, completely or at least partially, within the memory 312 and/or within the CPU 306 during execution thereof by the computing device 300. The memory 312 and the CPU 306 also can constitute machine-readable media. The term "machine-readable media", as used here, refers to a single medium or multiple media (e.g., a centralized or distributed database, and/or associated caches and servers) that store the one or more sets of instructions 320. The term "machine-readable media", as used here, also refers to any medium that is capable of storing, encoding or carrying a set of instructions 320 for execution by the control system 300 and that cause the control system 300 to perform any one or more of the methodologies of the present disclosure.

In some scenarios, the hardware entities 314 include an electronic circuit (e.g., a processor) programmed for facilitating control over the robotic arm. In this regard, it should be understood that the electronic circuit can access and run application(s) 324 installed on the computing device 300.

Figure 4:
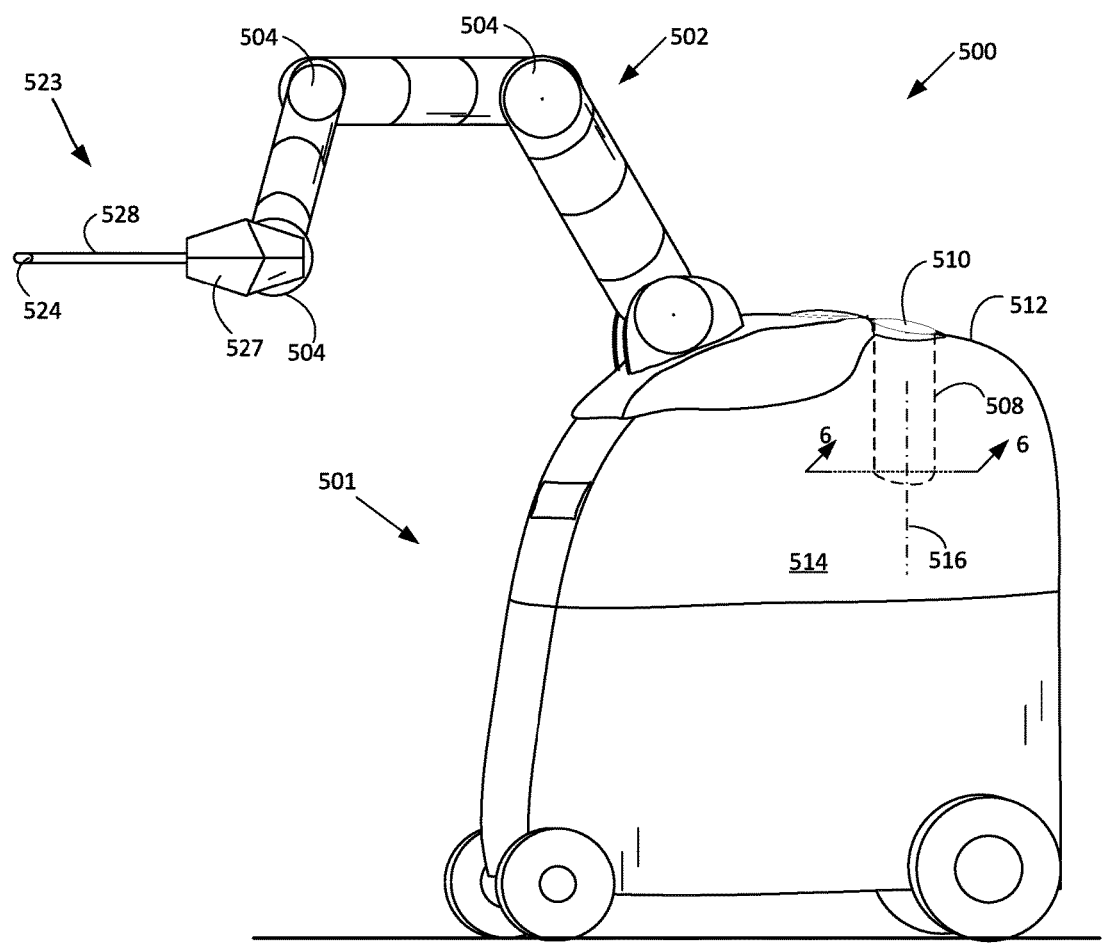
FIG. 4 is a drawing that is useful for understanding a portable robotic IORT system with a calibration well.
Figure 5:
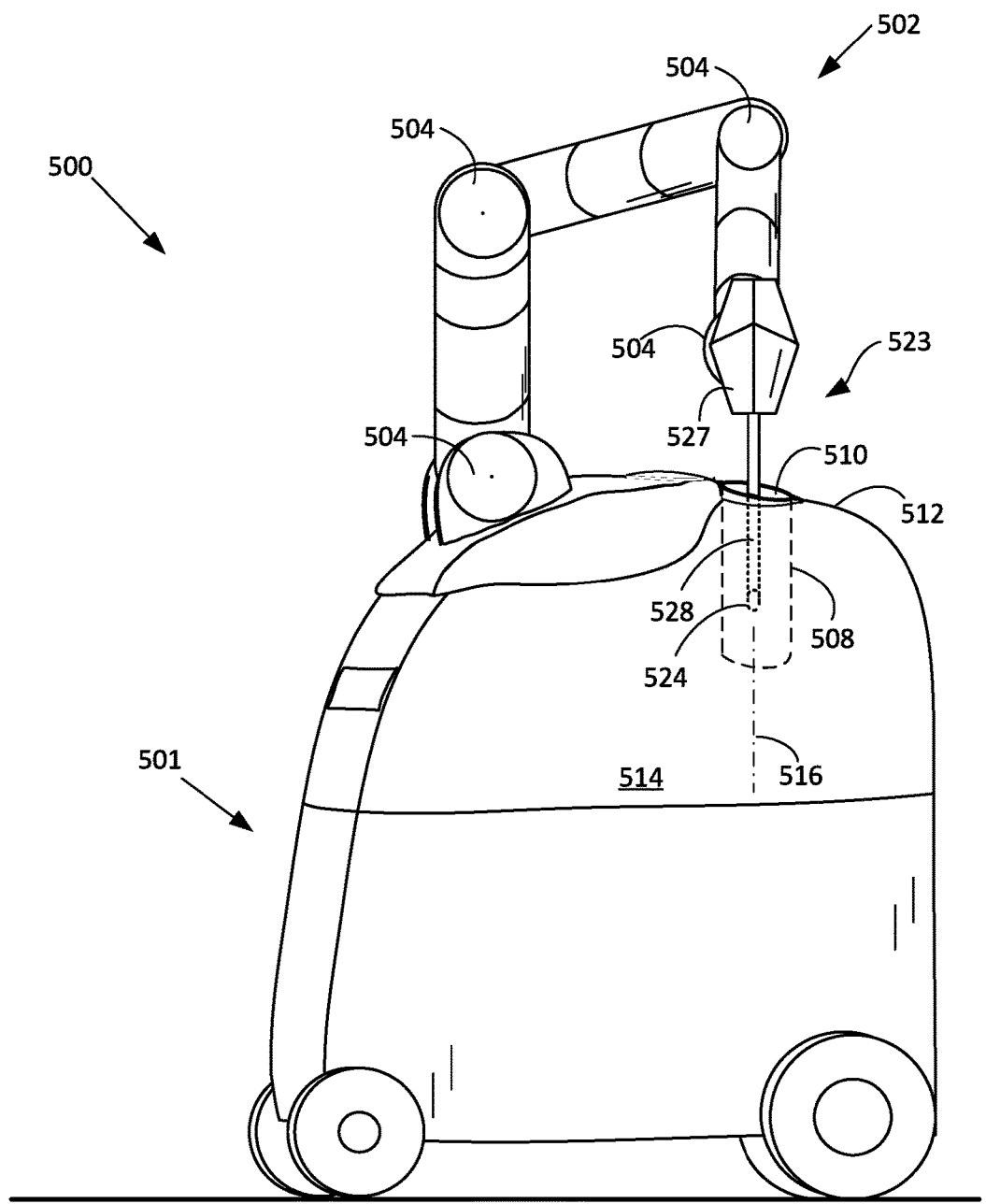
FIG. 5 is a drawing that is useful for understanding a portable robotic IORT system with a calibration well in which an X-ray treatment head is inserted for calibration.

FIGS. 4 and 5 are drawings which are useful for understanding how a calibration well 508 can be integrated in or on an robotic IORT X-ray system 500. Robotic IORT X-ray system 500 is similar to the robotic IORT X-ray systems described in FIG. 1-3. The IORT X-ray system 500 includes a base unit 501 on which a robotic arm 502 is mounted. The robotic arm includes a plurality of joints 504. The system also includes an IORT radiotherapy component which is comprised of head unit portion 523. The head unit portion is comprised of a main body 527, an elongated applicator body 528, and a treatment head 524. As shown in FIGS. 4 and 5, the X-ray system 500 further includes a calibration well 508. In some scenarios, the calibration well 508 can extend in a direction aligned with a vertical axis 516. However, the alignment direction of the calibration well 508 is not critical. Accordingly, the calibration well 508 could also be aligned with an axis that extends in a different direction and any such alternative alignment direction is contemplated as an acceptable variation, provided that the location is accessible to the robotic arm.

The location of calibration well 508 and the alignment of axis 516 are chosen so that the X-ray treatment head 524 can be automatically inserted into the calibration well 508 by the robotic arm 502. As such, the calibration well 508 will advantageously have a port 510 which provides access to the interior of the calibration well. The port 510 can be located at the top surface 511 of the base unit 501 as shown, or in a side wall 514 of the base unit 501. FIG. 4 shows the robotic arm with a plurality of joints 504 adjusted so that the X-ray treatment head 524 is ready for insertion into a treatment cavity of a patient (not shown) who is to undergo IORT treatment. FIG. 5 shows the robotic arm 502 with the plurality of joints 504 adjusted so that the treatment head 524 is inserted into the calibration well 508 for certain calibration operations.

Figure 6:
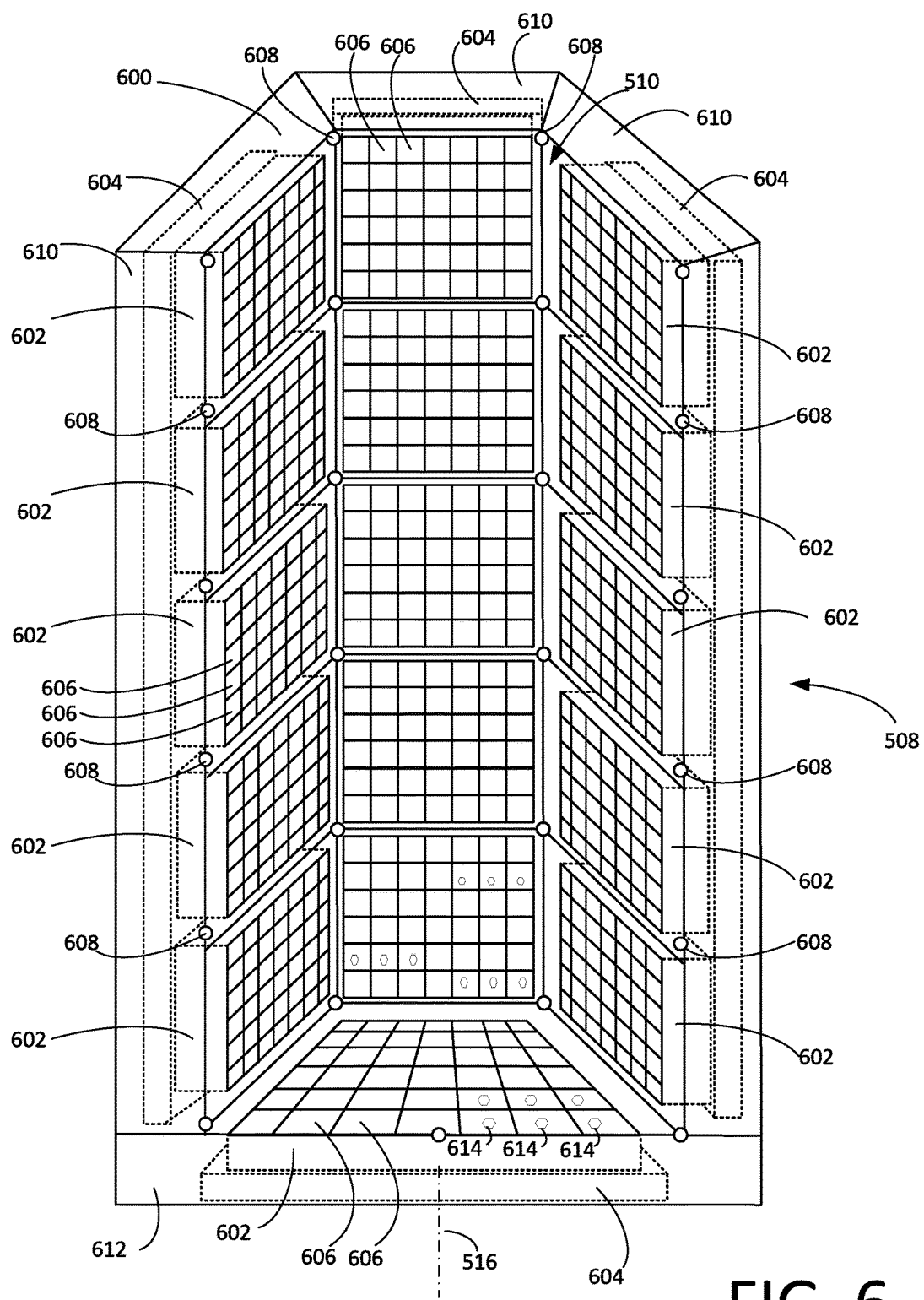
FIG. 6 is a cutaway view which shows certain features of an X-ray calibration well.

FIG. 6 is a cross-sectional view of the calibration well 508, taken along line 6-6 in FIG. 4. The calibration well 508 is formed from a well cavity structure 600 which defines an interior of the calibration well. In some scenarios, the interior of the calibration well can have a tubular configuration formed of one or more side walls 610 which extend in the direction parallel to axis 516 from the port 510 to an opposing bottom wall 612. A cross-sectional profile of the calibration well will depend on the number of side walls 610 which are used to form the calibration well. For example, in some scenarios six side walls can be used to form the well cavity structure such that the calibration well can have a hexagonal cross-sectional profile. The exact number of side walls is not critical. More or fewer sidewalls can be provided such that the cross-sectional profile of the calibration well can define a regular polygon such as a triangle, a square, a pentagon, a hexagon or an octagon. In other scenarios, the cross-sectional profile of the calibration well can be substantially circular so that the well is approximately cylindrical in shape. A bottom wall 612 can enclose an end of the calibration well opposed from the port 510.

The calibration well 508 will comprise a plurality of XRSE which are arranged on the interior faces which define the well cavity structure. The XRSE can include various different types of sensors which are selected for measuring X-ray beam intensity and/or an X-ray beam pattern produced by an X-ray treatment head 524. For example, in some scenarios, the XRSE can comprise a plurality of thermoluminescent dosimeter (TLD) arrays 602 which are distributed around the interior of the calibration well. In some scenarios, the plurality of TLD arrays can be disposed on a plurality of printed wiring boards (PWB) 604. TLDs are advantageous for such applications because they are small in size and relatively inexpensive, therefore many TLD sensory elements can be exposed to the radiation in a single exposure.

TLD arrays 602 are well known in the art and therefore will not be described here in detail. However, it should be understood that each TLD array 602 is comprised of a plurality of TLD sensory elements 606 arranged in a grid or array pattern. The TLD sensor elements 606 measure ionizing radiation exposure. TLD sensory elements produce or emit optical energy (e.g., visible light) from a crystal in the detector when the crystal is heated. The intensity of optical emission is dependent upon the X-ray radiation exposure. Each sensory element can include a photo-detector 610 which measures the intensity of the optical emission from the sensory element. In some scenarios, these photodetectors can be electrically connected to the printed wiring boards 604 so that the measured sensor data can be buffered and communicated to a computer processor (e.g. an IORT system control component 110).

Figure 7:
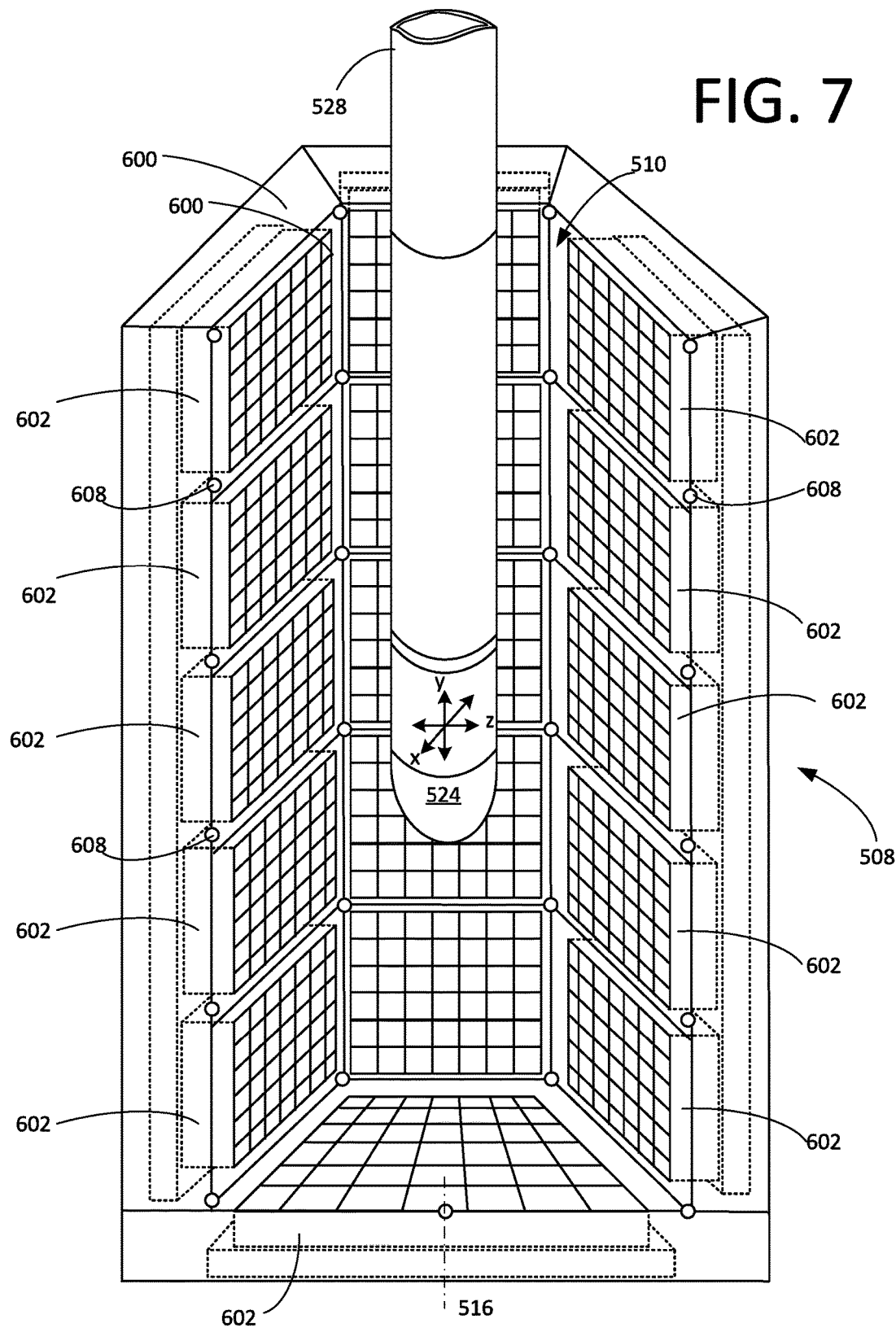
FIG. 7 shows the X-ray calibration well of FIG. 6 with an X-ray treatment head inserted therein.
Figure 8:
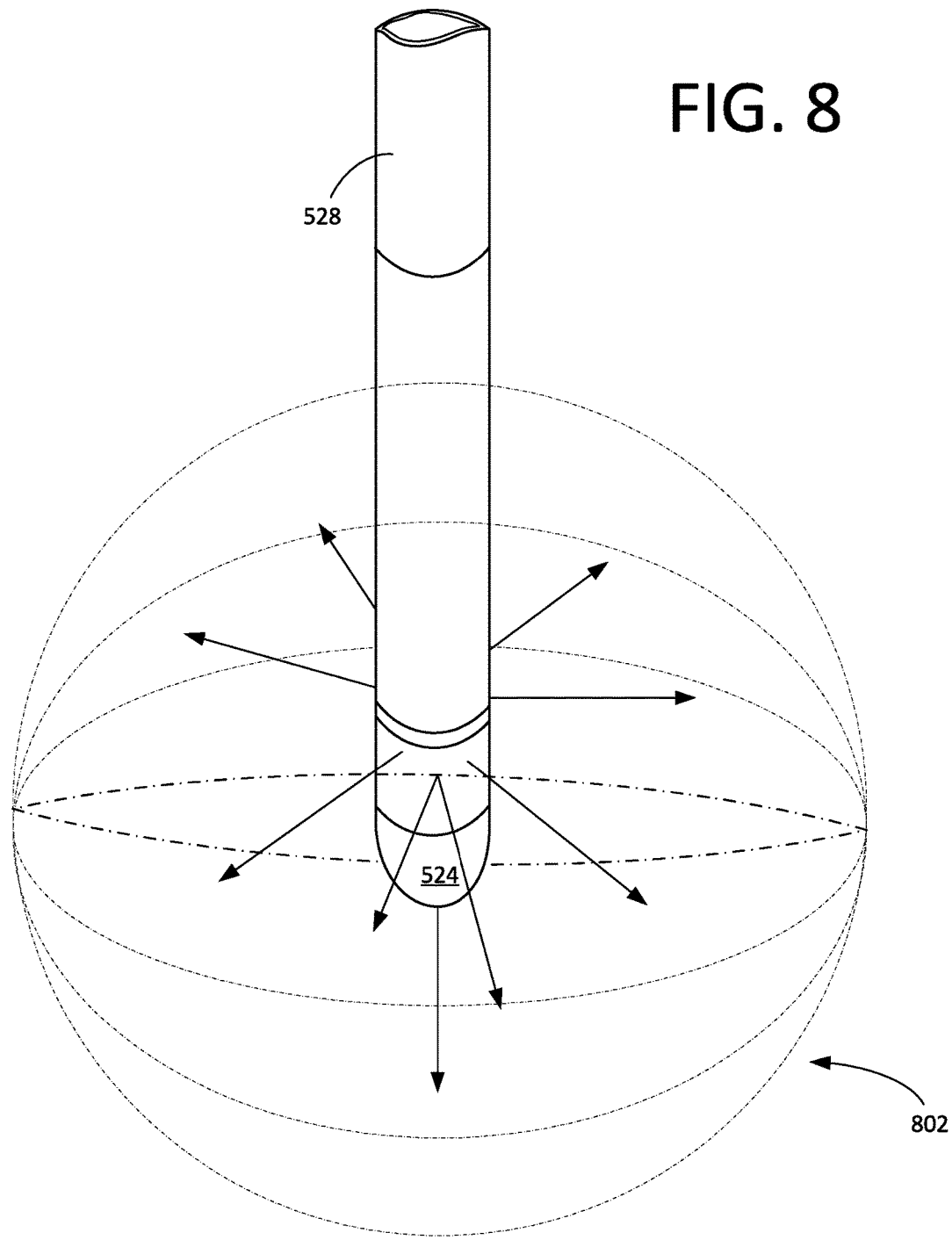
FIG. 8 shows a first exemplary X-ray radiation pattern from a X-ray treatment head.
Figure 9:
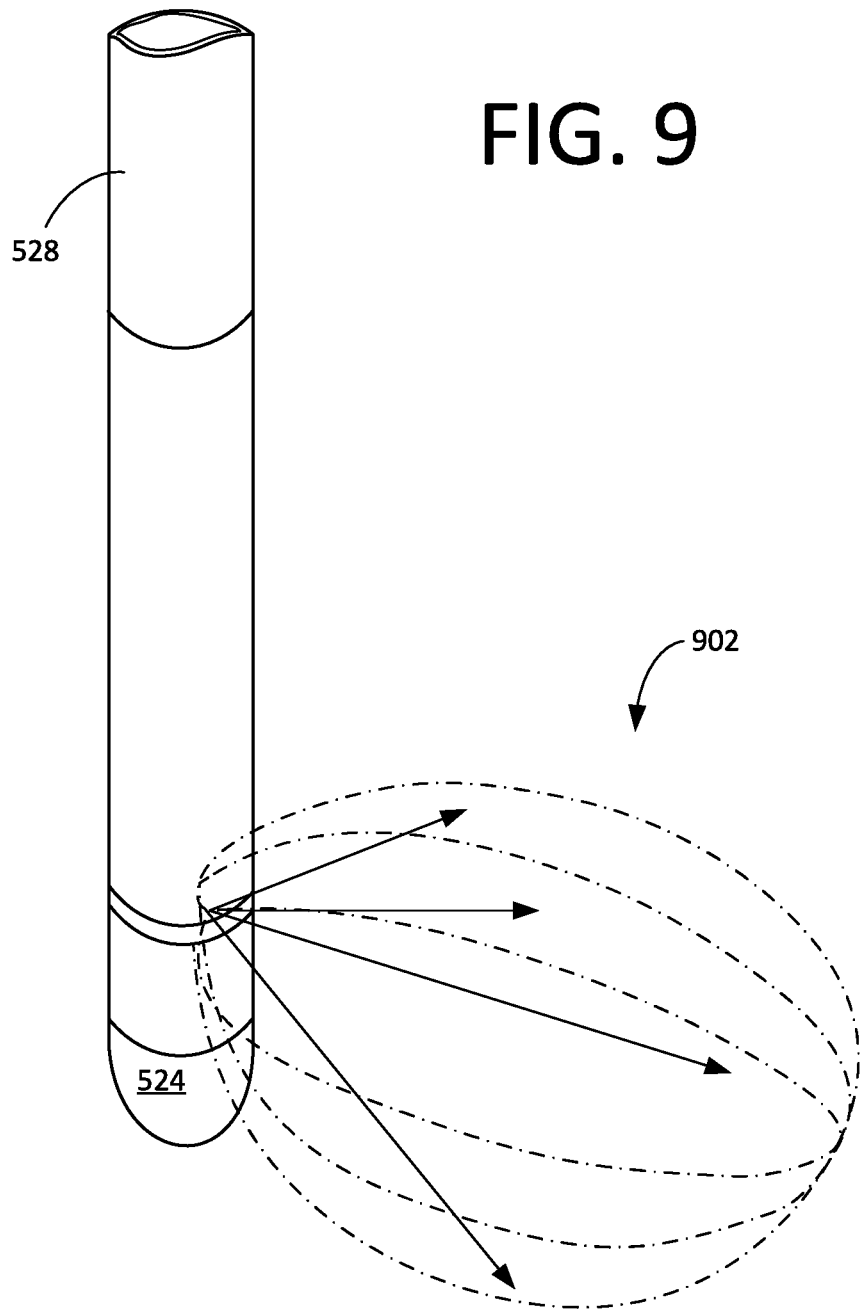
FIG. 9 shows a second exemplary X-ray radiation pattern from a X-ray treatment head.

The outputs from all of photo-detectors can be analyzed to obtain an instantaneous measure of the X-ray beam intensity in each direction relative to an origin point defined by the X-ray treatment head 524. Note that the presence of sensing elements on bottom wall 612 can facilitate beam sensing in directions that are axial with respect to the X-ray applicator (i.e. aligned with axis 516). The information from all of the XRSE can be useful for modeling the relative shape or pattern of the X-ray beam produced by a treatment head 524 which has been disposed in the calibration well 508 as shown in FIG. 7. For example, FIGS. 8 and 9 show two different beam patterns 802, 902 produced by a treatment head 524. The shape of the pattern and the absolute intensity or energy of each pattern can be measured using the calibration well.

As is known, TLD's are not ideal for absolute energy measurements. To facilitate absolute measurements of X-ray energy emitted by the X-ray applicator additional XRSE elements, such as ion chambers 608 can be used. An ionization chamber measures the charge from the number of ion pairs created within a gas caused by incident radiation. When exposed to X-ray radiation, an ionization current can flow between two electrodes and a magnitude of this ionization current can be converted to sensor data. Ion chambers are very accurate and precise measurement devices. Accordingly, they can effectively be used for beam calibration. The magnitude of the ionization current in the ion chamber can be determined by current measurement circuitry associated with the printed wiring boards 604. This current magnitude can be converted to digital data and then communicated to a computer processor (e.g. an IORT system control component 110). Other types of XRSE can be used in place of or in addition to the TLD and/or ion chamber sensors described above. For example, diode based X-ray measurement systems, can also be used in some scenarios. In fact, any type of XRSE now known or known in the future can be used in the calibration well for sensing the X-ray energy emitted by the treatment head.

The X-ray beam information sensed by the XRSE is communicated back to the IORT system control component which uses the collected data to generate a model of the X-ray beam. The resulting X-ray beam direction, shape and intensity in each system configuration can thus be modeled by the control system immediately before the system is used for IORT intervention. Based on this model, the control system can cause the X-ray generating system to selectively modify the operations of the robotic IORT system. For example, the control component can selectively control the X-ray generating system so that it is caused to generate X-ray energy at various intensity levels, and/or in different beam configurations. In other scenarios, the information can be used as a basis to control the robotic arm.

Figure 10:
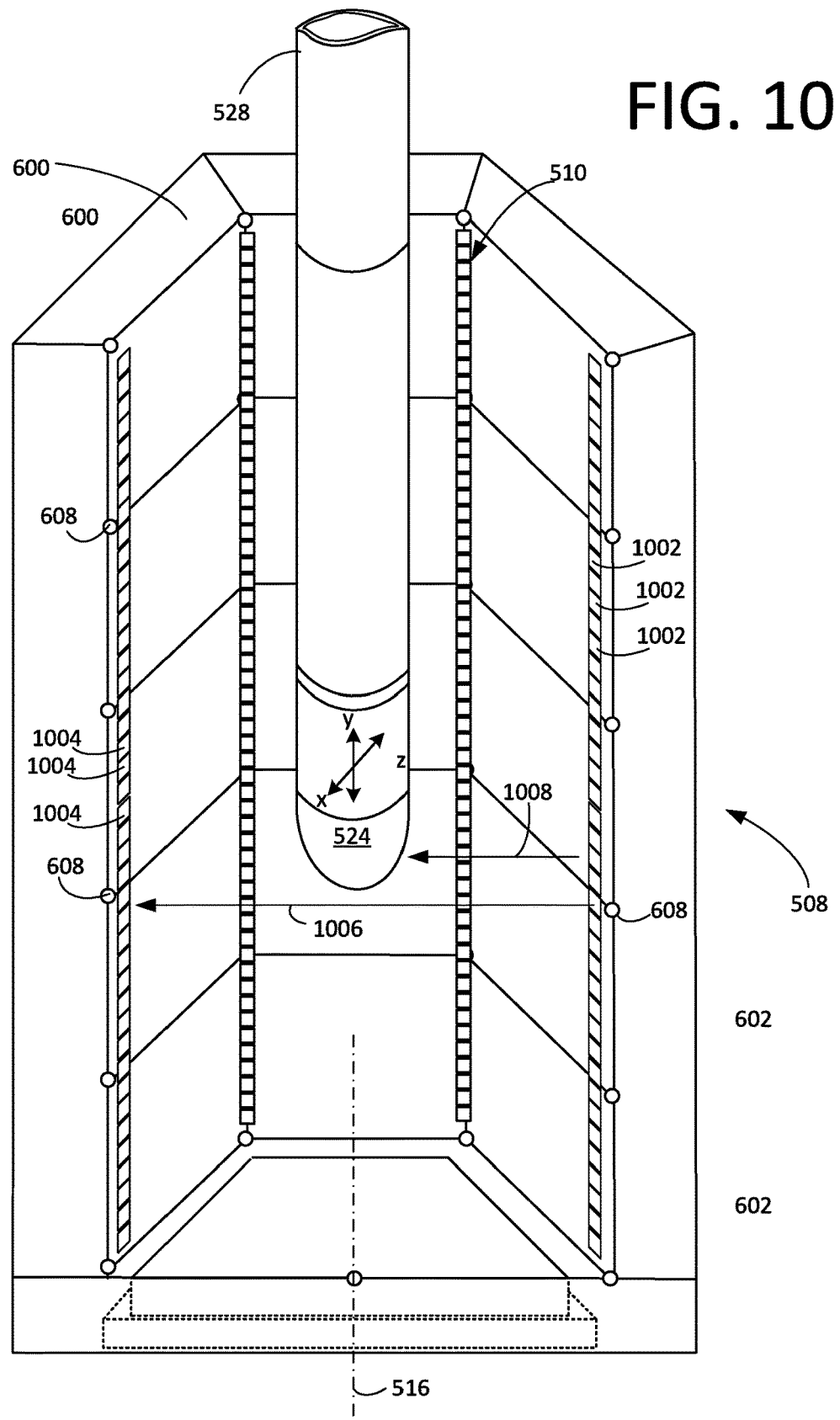
FIG. 10 shows a position sensing system which can be incorporated into the calibration well.

Referring now to FIG. 10, the interior of the calibration well is shown with certain components omitted for greater clarity. The interior of the calibration well can further comprise a sensor system which is configured to detect a position of the X-ray treatment head 524 when disposed within the calibration well. For example, the sensors can be comprised of a linear array of optical emitters 1002 and an opposing linear array of optical receivers 1004. When the X-ray treatment head 524 is not present in the calibration well, each optical receiver 1004 can receive an optical signal 1006 from a corresponding emitter element 1002. However, when the X-ray treatment head is present, the optical signal 1008 from an optical emitter 1002 is blocked so no optical signal is received at the optical receiver 1004. Accordingly, by detecting which optical receivers are receiving an optical signal, and which optical receivers are not receiving an optical signal, a depth of the X-ray treatment head 524 within the well can be detected. This arrangement can serve to verify the presence of the X-ray treatment head in the well before X-ray emissions are initiated. It can also serve as a means to check that the X-ray treatment head corresponds to the position as understood by the robotic control system. So the optical emitter/receiver arrangement can serve as a system check to verify the operational integrity of the robotic control system, before beginning IORT operations. Similarly, by carefully selecting the locations of the optical emitters and the optical receivers, the optical array can be further optimized to facilitate a determination that the treatment head 524 is properly positioned within the calibration well.

Of course, the optical system described merely represents one possible example of a sensing system for detecting the location of the X-ray applicator within the calibration well. A wide variety of other position systems are well known in the art and could be used to similar effect. All such systems now known or known in the future are contemplated for use in the present disclosure.

Figure 11:
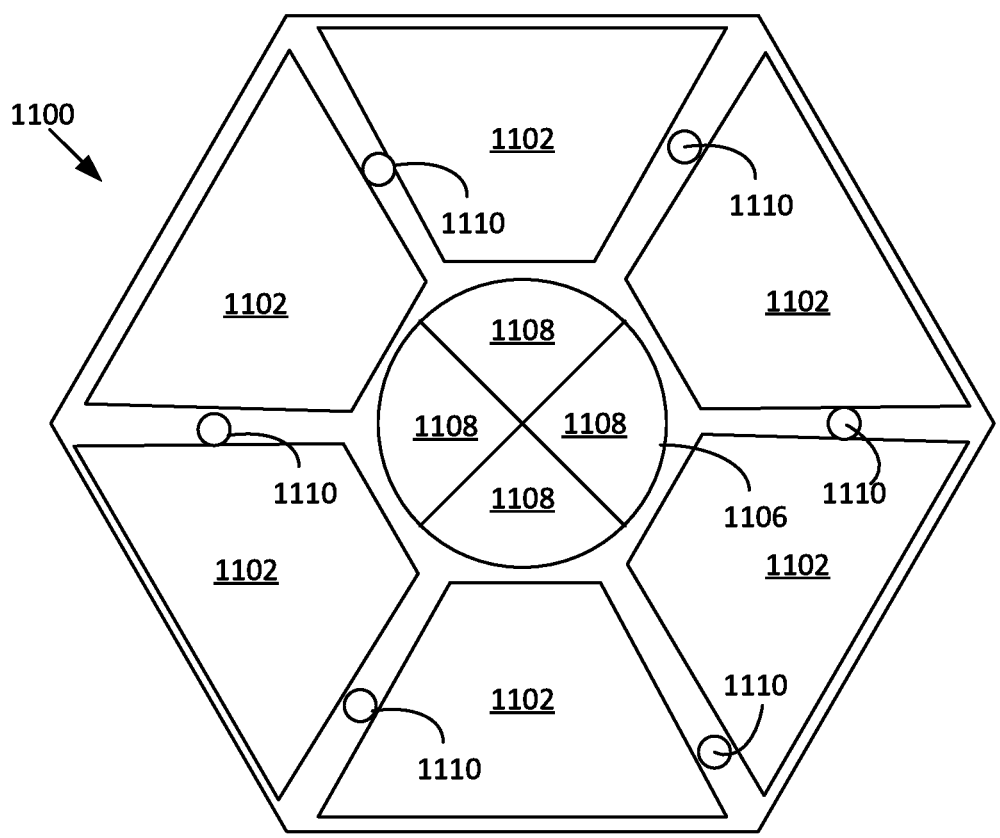
FIG. 11 shows a cover system which can be included at a port of the calibration well.

The port of the calibration well can be entirely open as shown in FIGS. 6 and 7. However, for safety reasons it can be advantageous in some scenarios to provide a cover system which would partially or completely enclose the port. Such a cover system could completely enclose the port 510 when the calibration well is not in use, but could be fully or partially opened when calibration operations are in progress. As an example, FIG. 11 shows a plan view of a cover 1100 as viewed from the interior of the calibration well 508. The cover 1100 can comprise a port 1106 which is sealed by a plurality of flexible elastomeric flaps 1108. The X-ray applicator can be inserted into the calibration well by pushing against the elastomeric flaps, thereby causing them to flex and permit the X-ray applicator to enter the calibration well. Around a periphery of the port 1106 a plurality of XRSE elements can be disposed. These XRSE can comprise one or more of TLD arrays 1102, ion chambers 1110 and/or any other suitable type of sensing element.

Figure 12:
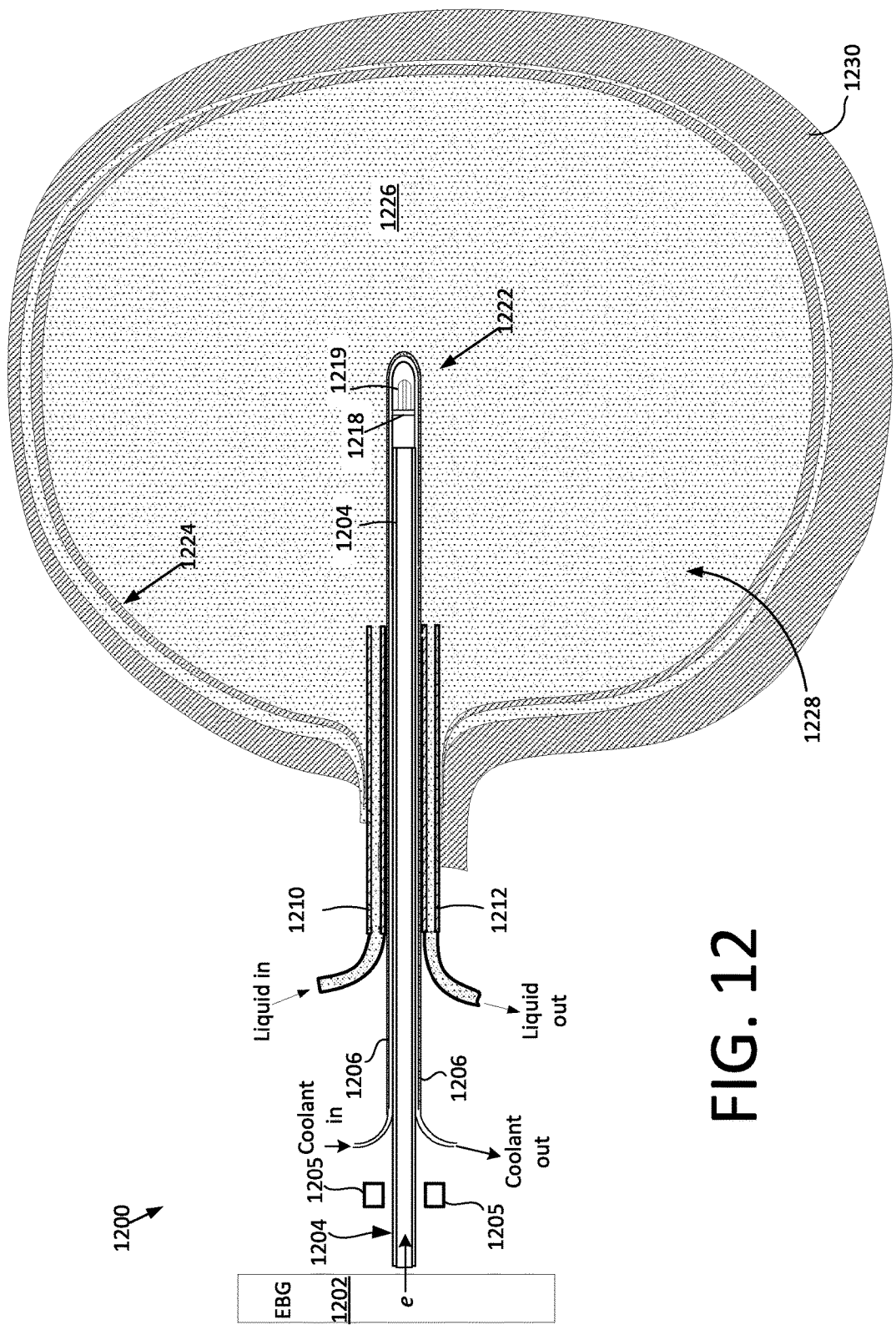
FIG. 12 shows a type of X-ray generating system which can be used with the portable robotic IORT system disclosed herein.

Turning now to FIG. 12 there is shown an alternative type of IORT X-ray source 1200 which can be used with the robotic IORT system described herein. This type of X-ray source is described in detail in U.S. patent application Ser. No. 15/941,547, filed Mar. 30, 2018, entitled Three-Dimensional Beam Forming X-ray Source, the disclosure of which is incorporated herein by reference. Briefly, the system comprises an electron beam gun (EBG) 1202 and a drift tube 1204 which is supported on an end of the robotic arm distal from the base. An IORT X-ray generating element 1222 resides at an end of the drift tube 1204, distal from the EBG. In some scenarios, the EBG 1202 can reside in a head unit portion 223, 523 of an IORT radiotherapy component as described in FIGS. 1-5. For example, the EBG can reside in a main body 227, 527 of the head unit, attached to a robotic arm 202, 502. In such a scenario, the elongated applicator body 228, 528 can be comprised of the drift tube 1204. Further, the treatment head 224, 524 can be comprised of the IORT X-ray generating element 1222.

The drift tube 1204 is comprised of a conductive material such as stainless steel. Alternatively, the drift tube can be comprised of a ceramic material such as alumina or aluminum nitride with a conductive inner lining. The hollow inner portion of the drift tube is maintained at a vacuum pressure (e.g. a suitable vacuum pressure for purposes of embodiments described herein can be in the range below about 10-5 torr or particularly between about 10-9 ton to 10-7 ton).

In the X-ray source shown in FIG. 12, electrons e comprising an electron beam are accelerated by the EBG toward an X-ray target 1218. These electrons will have significant momentum when they arrive at the entry aperture of the drift tube. The hollow interior of the drift tube is maintained at a vacuum pressure and at least the inner lining of the tube is maintained at ground potential. Accordingly, the momentum imparted to the electrons by EBG 1202 will continue to ballistically carry the electrons down the length of the drift tube at very high velocity (e.g. a velocity approaching the speed of light) toward the X-ray target 1218. It will be appreciated that as the electrons are traveling along the length of the drift tube 1204, they are no longer electrostatically accelerated. When the electrons impact upon the X-ray target 1218, X-rays are generated. Details of the beam steering and sculpting are beyond the scope of this disclosure. However, it is noted that the direction and shape of the X-ray beam can be sculpted or varied by using electromagnetic steering coils 1205 to vary which portion of the X-ray target 1218 is impacted by the electrons that comprise the electron beam. This steering process can be facilitated by a scepter element 1219 which is disposed adjacent to the X-ray target 1218.

The X-ray target 1218 is comprised of a disk-shaped element which is disposed transverse to the direction of electron beam travel. For example, the disk-shaped element can be disposed in a plane which is approximately orthogonal to the direction of electron beam travel. In some embodiments, the X-ray target 1218 can enclose an end portion of the drift tube distal from the EBG 1202 to facilitate maintenance of the vacuum pressure within the drift tube. The X-ray target 1218 can be almost any material, however it is advantageously comprised of a material such as molybdenum, gold, or tungsten which has a high atomic number so as to facilitate the production of X-rays at relatively high efficiency when bombarded with electrons.

An interstitial space between the X-ray generating element 1222 and a wound cavity defined by a tissue wall 1230 can be filled with saline fluid 1226 disposed within a fluid bladder 1224. The fluid bladder can be an elastic balloon-like member which is inflated with the fluid 1226 so as to fill an interstitial space 1228 between the X-ray source and a tissue wall 1230 (e.g. a tissue wall comprising a tumor bed). Fluid conduits 1210, 1212 disposed in or on the robotic arm can facilitate a flow of fluid to and from the interior of the fluid bladder. Such an arrangement can help enhance the uniformity of irradiation of the tumor bed by positioning the entire tissue wall a uniform distance away from the X-ray source to facilitate a more consistent radiation exposure. The generation of X-rays at X-ray target 1218 can generate substantial amounts of heat. So in addition to the fluid 1226 which fills the interstitial space, a separate flow of coolant can be provided to the treatment head through coolant conduits 1206.

The various components comprising the X-ray source 1200 (e.g., EBG 1202, the drift tube 1204, and treatment head 1222) can be mounted on the robotic arm as shown in FIGS. 4 and 5. The position of the X-ray source can be controlled by the robotic arm so that movement of the X-ray source is coordinated with natural body motion (e.g. breathing movement) of the patient undergoing treatment.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

I claim:

1. An IORT X-ray delivery system comprising:
a portable base unit;
a robotic arm;
a first end of the robotic arm mounted to the portable base unit;
an X-ray treatment head disposed on a second end of the robotic arm distal from the first end;
the X-ray treatment head comprising at least one X-ray component configured to generate therapeutic radiation in the X-ray wavelength range;
a calibration well disposed at a predetermined location in the portable base unit, the calibration well comprised of a recess into which the X-ray treatment head can be received and having at least one port through which the X ray treatment head can be inserted by the robotic arm for calibration operations; and
wherein the calibration well includes a plurality of X-ray radiation sensing elements (XRSE) disposed at distributed locations around a periphery of the calibration well.

2. The IORT X-ray delivery system according to claim 1, further comprising a control system configured to perform at least one calibration process including a positioning operation in which the robotic arm is controlled by the control system to insert the X-ray treatment head through the at least one port so that the X-ray treatment head is disposed at a predetermined calibration location inside the calibration well.

3. The IORT X-ray delivery system according to claim 2, wherein the control system is configured to control the at least one X-ray component to produce an X-ray emission having a beam pattern, during a time when the X-ray treatment head is disposed at the predetermined calibration location.

4. The IORT X-ray delivery system according to claim 3, wherein the control system is responsive to sensing data received from the plurality of XRSE, to determine at least one of a measured intensity and a measured beam pattern of X-ray radiation produced by the X-ray treatment head as a result of the X-ray emission.

5. The IORT X-ray delivery system according to claim 4, wherein the control system is configured to compare the measured beam pattern to a specified beam pattern.

6. The IORT X-ray delivery system according to claim 5, wherein the control system is configured to modify at least one operating parameter of the IORT X-ray deliver system responsive to the comparison by the control system of the measured beam pattern to specified beam pattern.

7. The IORT X-ray delivery system according to claim 6, wherein the at least one operating parameter is a duration of a treatment time during which a therapeutic dose of X-ray radiation is delivered.

8. The IORT X-ray delivery system according to claim 6, wherein the at least one operating parameter is a beam control parameter which determines at least one of a main beam direction, a main beam intensity, and a shape of the beam pattern.

9. The IORT X-ray delivery system according to claim 6, wherein the at least one operating parameter is a robotic arm control parameter which determines a static position of the X-ray treatment head to be used when a therapeutic dose of X-ray radiation is applied.

10. The IORT X-ray delivery system according to claim 6, wherein the at least one operating parameter is a motion control parameter which defines a dynamic movement of the robotic arm to be performed while a therapeutic dose of X-ray radiation is applied.

11. The IORT X-ray delivery system according to claim 10, wherein the dynamic movement is a movement or a change of orientation which minimizes variations in the therapeutic dose delivered by the treatment head to surfaces of a tumor bed.

12. A method for calibrating an IORT X-ray delivery system comprising: supporting a first end of a robotic arm on a portable base unit;
supporting on a second end of the robotic arm an X-ray treatment head comprising at least one X-ray component configured to generate therapeutic radiation in the X-ray wavelength range;
using a control system to:
cause the robotic arm to insert the X-ray treatment head in a calibration well that is defined by a recess provided at a predetermined location in the portable base unit;
activate the at least one X-ray component to generate an X-ray emission from the X-ray treatment head while the X-ray treatment head is disposed at a predetermined calibration location in the calibration well;
receive sensor data from a plurality of X-ray radiation sensing elements (XRSE) disposed at distributed locations around a periphery of the calibration well; and
using the sensor data to determine at least one of an intensity and a beam pattern of X-ray radiation produced by the X-ray treatment head.

13. The method according to claim 12, further comprising using the control system to automatically compare the determined beam pattern to a specified beam pattern.

14. The method according to claim 13, further comprising operating the control system to automatically modify at least one operating parameter of the IORT X-ray delivery system responsive to the comparison by the control system of the determined beam pattern to a specified beam pattern.

15. The method according to claim 14, further comprising selecting the at least one operating parameter to include a duration of a treatment time during which a therapeutic dose of X-ray radiation is delivered.

16. The method according to claim 14, further comprising selecting the at least one operating parameter to include a beam control parameter which determines at least one of a main beam direction, a main beam intensity, and a shape of the beam pattern.

17. The method according to claim 14, further comprising selecting the at least one operating parameter to include a robotic arm control parameter which determines a static position of the X-ray treatment head to be used when a therapeutic dose of X-ray radiation is applied.

18. The method according to claim 14, further comprising selecting the at least one operating parameter to include a motion control parameter which defines a dynamic movement of the robotic arm to be performed while a therapeutic dose of X-ray radiation is applied.

19. The method according to claim 18, wherein the dynamic movement minimizes variations in the therapeutic dose delivered by the treatment head to surfaces of a tumor bed.

20. The method according to claim 18, wherein the dynamic movement is selected to change an orientation of the treatment head.

* * * * *